(12) United States Patent
Ozarslan et al.

(10) Patent No.: US 8,704,515 B2
(45) Date of Patent: Apr. 22, 2014

(54) MAGNETIC RESONANCE SPECIMEN EVALUATION USING MULTIPLE PULSED FIELD GRADIENT SEQUENCES WITH A WAVENUMBER MAGNITUDE LOCAL MINIMUM AND RESTRICTED COMPARTMENT ESTIMATION

(75) Inventors: Evren Ozarslan, Bethesda, MD (US); Peter J. Basser, Washington, DC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1017 days.

(21) Appl. No.: 12/539,462

(22) Filed: Aug. 11, 2009

(65) Prior Publication Data

US 2010/0033182 A1 Feb. 11, 2010

Related U.S. Application Data

(60) Provisional application No. 61/087,968, filed on Aug. 11, 2008.

(51) Int. Cl.
*G01R 33/44* (2006.01)
*A61B 5/05* (2006.01)

(52) U.S. Cl.
USPC ............ 324/309; 324/307; 324/318; 600/410

(58) Field of Classification Search
USPC .......................... 324/300–322; 600/407–435; 382/128–131
See application file for complete search history.

(56) References Cited

U.S. PATENT DOCUMENTS

| 4,723,536 | A  | * | 2/1988 | Rauscher et al. | 600/14 |
|---|---|---|---|---|---|
| 4,889,526 | A  | * | 12/1989 | Rauscher et al. | 600/14 |
| 5,786,692 | A  | * | 7/1998 | Maier et al. | 324/307 |
| 6,268,726 | B1 | * | 7/2001 | Prammer et al. | 324/303 |
| 6,362,619 | B2 | * | 3/2002 | Prammer et al. | 324/303 |
| 6,411,087 | B1 | * | 6/2002 | Fan et al. | 324/303 |
| 6,479,996 | B1 | * | 11/2002 | Hoogeveen et al. | 324/309 |
| 6,583,621 | B2 | * | 6/2003 | Prammer et al. | 324/303 |
| 6,711,430 | B1 | * | 3/2004 | Ferris et al. | 324/318 |
| 6,825,659 | B2 | * | 11/2004 | Prammer et al. | 324/303 |

(Continued)

OTHER PUBLICATIONS

Callaghan, "A simple matrix formalism for spin echo analysis of restricted diffusion under generalized gradient waveforms," J. Mag. Reson., 129:74-84 (1997).
Caprihan et al., "A multiple-narrow-pulse approximation for restricted diffusion in a time-varying field gradient," J. Magn. Reson. A, 118:94-102 (1996).

(Continued)

*Primary Examiner* — Melissa Koval
*Assistant Examiner* — Tiffany Fetzner
(74) *Attorney, Agent, or Firm* — Klarquist Sparkman, LLP

(57) ABSTRACT

Using pulsed-field-gradient (PFG) sequences, the sizes of the pores in ordered porous media can be estimated from the "diffraction" pattern that the signal attenuation curves exhibit. A different diffraction pattern is observed when the experiment is extended to a larger number (N) of diffusion gradient pulse pairs. Differences in the characteristics of attenuation curves also permit distinguishing different pore shapes and distributions using the N-PFG technique. Using an even number of PFG pairs, an approximation to the average pore size can be obtained even when the sample contains pores with a broad distribution of sizes. Multi-PFG sequences can also be used to differentiate free and multi-compartment diffusion, and to estimate compartment sizes and orientations, and to distinguish microscopic and ensemble anisotropy.

16 Claims, 25 Drawing Sheets

(56) References Cited

U.S. PATENT DOCUMENTS

| | | | | |
|---|---|---|---|---|
| 6,873,153 B2* | 3/2005 | Frydman | .................. | 324/307 |
| 6,873,156 B2* | 3/2005 | Ferris et al. | .................. | 324/318 |
| 7,053,611 B2* | 5/2006 | Freedman | .................. | 324/303 |
| 7,180,288 B2* | 2/2007 | Scheven | .................. | 324/303 |
| 7,253,618 B1* | 8/2007 | Freedman et al. | ............ | 324/303 |
| 7,271,588 B2* | 9/2007 | Frydman | .................. | 324/318 |
| 7,408,346 B2* | 8/2008 | Szyperski et al. | ............ | 324/307 |
| 7,643,863 B2* | 1/2010 | Basser et al. | ................ | 324/307 |
| 7,894,891 B2* | 2/2011 | Song et al. | .................. | 600/546 |
| 8,380,280 B2* | 2/2013 | Basser et al. | ................ | 600/410 |
| 2001/0045829 A1* | 11/2001 | Prammer et al. | ............ | 324/303 |
| 2002/0163335 A1* | 11/2002 | Prammer et al. | ............ | 324/303 |
| 2003/0164703 A1* | 9/2003 | Ferris et al. | .................. | 324/318 |
| 2004/0124837 A1* | 7/2004 | Prammer et al. | ............ | 324/303 |
| 2005/0007100 A1* | 1/2005 | Basser et al. | ................ | 324/200 |
| 2005/0007111 A1* | 1/2005 | Frydman | .................. | 324/307 |
| 2005/0134275 A1* | 6/2005 | Frydman | .................. | 324/321 |
| 2006/0097722 A1* | 5/2006 | Scheven | .................. | 324/303 |
| 2007/0007959 A1* | 1/2007 | Szyperski et al. | ............ | 324/307 |
| 2007/0238969 A1* | 10/2007 | Song et al. | .................. | 600/410 |
| 2009/0010517 A1* | 1/2009 | Basser et al. | ................ | 382/131 |
| 2010/0033182 A1* | 2/2010 | Ozarslan et al. | ............ | 324/309 |
| 2011/0105886 A1* | 5/2011 | Song et al. | .................. | 600/410 |

OTHER PUBLICATIONS

Partha P. Mitra, "Multiple wave-vector extensions of the NMR pulsed-field-gradient spin-echo diffusion measurement," Phys. Rev. B, 51(21):15074-15078 (1995).

Ozarslan et al., "Generalized Diffusion Tensor Imaging and Analytical Relationships Between Diffusion Tensor Imaging and High Angular Resolution Diffusion Imaging," Mag. Res. Med., 50:955-965 (2003).

Ozarslan et al., "Resolution of complex tissue microarchitecture using the diffusion orientation transform (DOT)," NeuroImage, 31:1086-1103 (2006).

Ozarslan et al., "MR diffusion/'diffraction' phenomenon in multi-pulse-field gradient experiments," J. Magn. Reson., 188(2):285-294 (2007).

Siegfried Stapf, "Determination of velocity autocorrelation functions by multiple data acquisition in NMR pulsed—field gradient experiments," J. Magn. Reson., 152:308-312 (2001).

Stepišnik et al., "The long time tail of molecular velocity correlation in a confined fluid: observation by modulated gradient spin-echo NMR," Physica B, 292:296-301 (2000).

Stepišnik et al., "Low frequency velocity correlation spectrum of fluid in a porous media by modulated gradient spin echo," Magn. Reson. Imaging, 19:469-472 (2001).

\* cited by examiner coexistence of ensemble anisotropy and microscopic anisotropy

MAGNETIC RESONANCE SPECIMEN EVALUATION USING MULTIPLE PULSED FIELD GRADIENT SEQUENCES WITH A WAVENUMBER MAGNITUDE LOCAL MINIMUM AND RESTRICTED COMPARTMENT ESTIMATION

CROSS-REFERENCE TO RELATED APPLICATIONS

This application claims priority from U.S. Provisional Application 61/087,968, filed Aug. 11, 2008, which is incorporated herein by reference. This application refers to U.S. patent application Ser. No. 12/114,713, filed May 2, 2008, which is also incorporated herein by reference.

STATEMENT OF GOVERNMENT RIGHTS

This invention was made with government support under a contract awarded by the Department of Health and Human Services, National Institutes of Health. The government has certain rights in the invention.

TECHNICAL FIELD

The disclosure pertains to methods and apparatus for magnetic resonance based evaluation of heterogeneous and other specimens.

BACKGROUND

Diffusion of spin bearing molecules in porous media observably affects the nuclear magnetic resonance (NMR) signal. Inferring microstructural features of the pore from the diffusion NMR signal attenuation has proven to be of paramount value in a variety of applications from oil-well logging and dynamics of polymers to the diagnosis and monitoring of many diseases in the human body. The most commonly used NMR method with which to observe diffusion in porous media employs the pulsed field gradient (PFG) experiments in which a pair of pulsed magnetic field gradients is applied to encode displacements between the application of these two pulses.

Although the PFG experiments have been useful in characterizing pore microstructure, many additional features, particularly those related to different length scales of porous media, can be gleaned if different pulse sequences are employed. One such alternative is the multi-PFG experiment, which involves the application of repeated pairs of diffusion gradients. Variants of this pulse sequence have been considered and found useful in various applications. The simplest version of such sequences employs only two pairs of gradients; a spin-echo version of this double-PFG sequence is shown in FIG. 1A. In FIG. 1A, each pulsed-gradient spin-echo (PGSE) block, comprising a pair of diffusion gradients of duration $\delta$, sensitizes the signal to motion that occurs during an interval $\Delta$. The movements of molecules during the two encoding intervals are correlated when the mixing time $t_m$ is finite. $G_1$ and $G_2$ denote the diffusion gradients of the first and second encoding blocks, respectively. FIG. 1B shows another double-PGSE sequence that results from the simultaneous application of the second and third gradients of the sequence in FIG. 1A.

The acquisition and analysis schemes for double-PFG data depend on the structure to be examined. For example, the strength of the first and second gradients can be independently varied. When the diffusion process can be characterized locally by a diffusion tensor, then a two-dimensional Laplace transform can be employed to generate maps of diffusion coefficients depicting the correlations of motion during the two encoding periods. This approach has been applied to plant tissue as well as various phases of liquid crystals.

The double-PFG experiments have received increasing attention recently due to the realization that such experiments are sensitive to restricted diffusion even at diffusion wavelengths that are long compared to the pore dimensions. As used herein, diffusion wavelength is defined as the quantity $\Lambda=(\gamma\delta G)^{-1}$, wherein $\gamma$ denotes the gyromagnetic ratio of the spins and G is the gradient magnitude. The long diffusion wavelength regime ($\Lambda^2 \gg a^2$, where a is a characteristic pore size) is sometimes referred to as the small-q regime, $(2\pi qa)^2 \ll 1$, where q denotes the wave number, defined through the relationship $q=1/(2\pi\Lambda)=\gamma\delta G/(2\pi)$.

The sensitivity of the double-PFG experiments to restricted diffusion in this regime is a very desirable property, which makes it possible to probe small pores using relatively small diffusion gradient strengths. Recent findings suggest that the dependence of the signal intensity on the angle between the two gradients, $G_1$ and $G_2$, may make it possible to determine the sizes of biological cells using moderate gradient strengths. Although such an angular dependence was predicted by P. P. Mitra, Phys. Rev. B 51:15074 (1995), Mitra considered only special limiting cases of the double-PFG experiment. ($|G_1|=|G_2|$, $\Delta \to \infty$, $\delta=0$ and $t_m=0$ or $t_m \to \infty$), which are difficult to achieve in practice. Moreover, when even one of these conditions is not fully met, systematic errors in the estimations of the microstructural features are unavoidable.

The observation of diffusion of spin-labeled molecules provides an indirect means to probe geometries whose characteristic dimensions are smaller than the voxel resolution of conventional noninvasive MR imaging techniques. Incorporation of pulsed field gradients in MR pulse sequences has made it possible to conveniently measure the diffusion characteristics of the sample. One striking observation was that in materials with an ordered structure, signal attenuation (when plotted as a function of $q=\gamma\delta G/2\pi$, where $\gamma$ is the gyromagnetic ratio, $\delta$ is the diffusion pulse duration and G is the gradient vector) exhibited non-monotonic behavior. Specifically, when the wave-number ($q=|q|$) assumed certain values depending on the spacing between the restrictions, there was an almost perfect phase cancellation resulting in very small signal values. This fact was exploited to determine the compartment size. Perhaps the simplest system that exhibits this behavior is diffusing molecules sandwiched between two infinite parallel planes separated by a distance L. For this geometry, the diffraction dips occur when the wave-vector takes the values q=n/L, where n=1, 2, 3, . . . is the index of the diffraction well.

Another observation regarding the diffraction patterns is that in anisotropic samples, if diffusion is almost free along certain directions but restricted along others, the diffraction pattern is very sensitive to the direction of the diffusion gradient; It is observed only when the diffusion gradients are almost perpendicular to the restricting walls. This fact can be exploited to estimate fiber orientations.

Despite its potential, the application of diffraction patterns has been limited mostly because of the demanding nature of the measurements. In particular, the q-value has been required to exceed the reciprocal of the spacing between restricting barriers. This can be achieved by increasing the magnitude of the diffusion gradients or their durations. However, hardware limitations prohibit increasing the gradient strength beyond a certain point. Although increasing the gradient duration is possible, the violation of the narrow pulse approximation pushes the diffraction dips towards even larger q-values which in turn makes the pore size estimations less accurate. Another characteristic of the diffraction patterns that limits their widespread use is that the diffraction wells are observable when the diffusion time is long. In short diffusion times, the signal attenuation curve is quite featureless. In contrast to the requirement on q described above, this makes it difficult to measure the sizes of larger pores.

Most porous materials of interest are composed of pores with a broad distribution of sizes. In this case the diffraction wells are not observable at all, and the estimation of an average pore size may be possible using sophisticated methods but not directly from the locations of the diffraction dips. This problem is especially important for the estimation of cell sizes in biological specimens because of their large variability. Consequently, the non-monotonicity of the MR signal has been observed only in the very coherently organized regions of biological tissue such as corpus-callosum of fixed rat brains.

Some PFG-based measurements have involved the inversion of the magnetization via the application of a series of subsequent 180° radio-frequency (RF) pulses and application of separate pairs of diffusion gradients before and after each of the RF pulses as shown in FIG. 1C, In FIG. 1C, $t_m$ denotes the waiting time between two consecutive pulsed-gradient spin-echo (PGSE) blocks. Typical applications of such pulse sequences are based on 'idealized' experimental conditions such as $\delta=0$, $\Delta\to\infty$ (wherein $\Delta$ is the diffusion pulse separation) and $t_m=0$ or $t_m\to\infty$. Such conditions are difficult or impossible to achieve in many practical applications.

SUMMARY

Disclosed herein are methods and apparatus that provide diffusion/diffraction-based specimen characterization (including imaging) using multiple PFG blocks or other pulse sequences. The disclosed methods can address the difficulties mentioned above, but the disclosed methods do not require any particular theory of operation or that any particular problem be solved.

In some examples, at least one computer readable medium is provided having stored thereon computer-executable instructions for a method that includes obtaining a recorded magnetic resonance signal as a function of magnetic resonance wavenumber in response to a multi-PFG sequence. An estimate of a distribution of restricted compartments of a sample is generated based on the magnetic resonance signal and the result is communicated or displayed to a user. Based on the estimate, the specimen can be assessed. In some examples, an estimate of a mean value of a restricted compartment size distribution is provided. In other examples, the estimate of the mean value is provided based on determination of a magnetic resonance wavenumber value associated with a local minimum value or zero crossing of the recorded magnetic resonance signal. In further examples, the multi-PFG sequence includes an odd number of PFG sequences. In other examples, the mean value is provided based on determination of a magnetic resonance wavenumber value associated with sign change in the recorded magnetic resonance signal. In still additional examples, the multi-PFG sequence includes an even number of PFG sequences. In some examples, the mean value is associated with a radius of cylindrical or spherical restricted compartments. In other examples, the PFG sequences of the multi-PFG sequence have common effective gradient magnitudes.

Representative methods comprise receiving a recorded magnetic resonance signal responsive to a multi-PFG sequence. Based on the recorded magnetic resonance signal, an estimate of at least one size characteristic of a distribution of restricted compartments in a specimen is provided. In some examples, the estimate is associated with a mean value of a size distribution and is based on a magnetic resonance wavenumber associated with a local minimum or a sign change of the recorded magnetic resonance signal.

Additional representative methods comprise applying at least a first PFG sequence and a second PFG sequence to a specimen, wherein the first and second sequences are applied with a plurality of angles between field gradients of the first and second sequences. A magnetic resonance signal as a function of the plurality of angles is recorded. Based on the recorded signal, an estimate of a dimension associated with a restricted compartment of the specimen is provided. In some embodiments, the dimension is associated with a distribution of restricted compartments of the specimen. In other examples, the dimension is associated with a diffusion distance that is a function of a diffusion constant in the restricted compartment. In further examples,an estimate of a restricted compartment distribution is provided. In further examples, an estimate of a-restricted compartment orientation is provided based on the recorded magnetic resonance signal or estimates of restricted compartment orientations for at least first and second restricted compartment distributions are provided. In some examples, an image is displayed that is based on restricted compartment properties as a function of specimen location. In some illustrative embodiments, the dimension is associated with a radius of a spherical or cylindrical restricted compartment. In other examples, the applied field gradients are selected so that product of a magnetic resonance wavenumbers and the estimated dimension is less than about 0.5. In additional examples, a plurality of recorded magnetic resonance signals as a function of angle is obtained, wherein the recorded signals are associated with a plurality of mixing times, diffusion times, or magnetic resonance wavenumbers.

BRIEF DESCRIPTION OF THE DRAWINGS

FIG. 3A illustrates dependence of the NMR signal intensity from spherical pores on the angle between the gradients used in the two encoding blocks of a double-PFG experiment. The specimen was assumed to contain 10,000 spheres whose radii were distributed with a Rician distribution of mean value $a_0$ and standard deviation $\sigma_a$. FIG. 3B illustrates the dependence of the signal intensity from a single sphere on the radius of the sphere.

In FIG. 4A, the gradient orientations and the orientation of the cylinder are along the z-axis. The direction of the first gradient is fixed along the x-axis. The orientation of $G_2$ is specified by the polar angle, $\theta$ and the azimuthal angle $\phi$. Note that with these definitions, the cosine of the angle between the two gradients is $\cos\psi=\sin\theta\cos\phi$. FIGS. 4B-4D illustrate signal attenuation from cylinders coherently oriented along the z-axis, cylinders with some angular dispersion where the mean orientation is along the z-axis, and cylinders with two distinct populations where the average orientation of one group is along the y-axis, that of the other group is along the z-axis, respectively. The surfaces displayed as insets in FIGS. 4C-4D illustrate the orientation distribution functions of the cylinders simulated.

FIG. 5A shows NMR signal attenuation with varying values of mixing time, wherein $\Delta=a^2/D_0$. FIG. 5B shows NMR signal attenuation with varying values of $\Delta$, wherein $t_m=0.002$ $a^2/D_0$.

In FIG. 12A, $\delta=(M-\frac{1}{2})\tau_a$ whereas in FIG. 12B, $\delta=M\tau_b$.

DETAILED DESCRIPTION

Disclosed herein are representative methods and apparatus based on the diffraction-like non-monotonicity of NMR signals in multi-PFG experiments. For example, when even numbers of diffusion gradient pulse pairs are used, the NMR signal typically becomes negative at about half the wave number necessary to observe the non-monotonicity in single-PFG experiments. Apart from the beneficial reduction of the necessary gradient strength, this zero-crossing also makes it possible to determine an average pore size more robustly, accurately and precisely even when the specimen under investigation contains pores with a broad distribution of sizes.

Figures 1A, 1B:
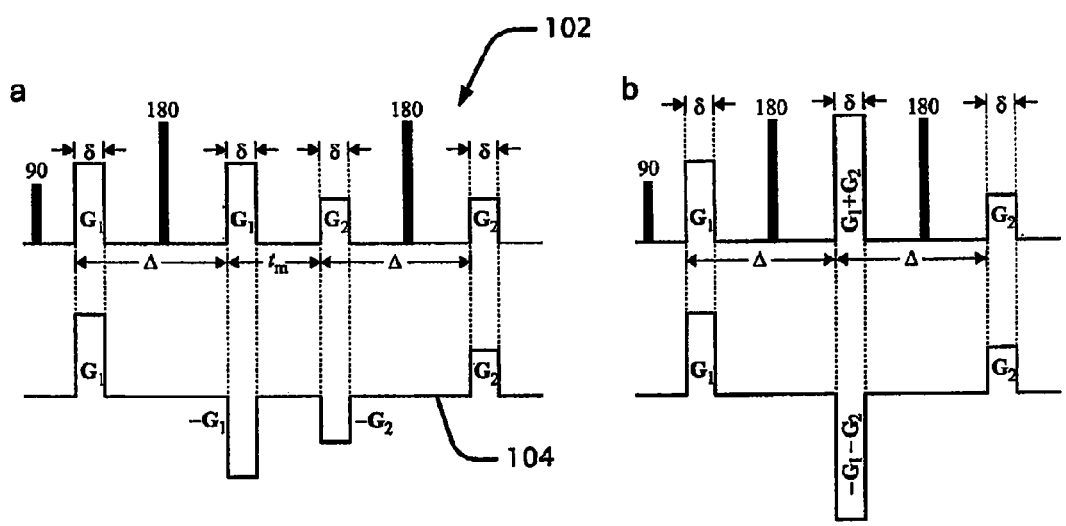
FIG. 1A illustrates a general double-PGSE pulse sequence 102. This pulse sequence features two distinct PGSE blocks separated from each other by a mixing time $t_m$. The pulse separation associated with each of the PGSE encodings is $\Delta$, where each diffusion gradient is assumed to have the same pulse length, $\delta$. A resulting effective gradient waveform 104 is also shown.
FIG. 1B illustrates a double-PGSE pulse sequence similar to that of FIG. 1A with the two middle gradients superposed. A mixing time is not defined for this pulse sequence.

This disclosure pertains to improved specimen characterization and analysis based on NMR signal intensity as a function of arbitrary parameters in double-PFG-based measurements. The disclosed methods and apparatus are particularly convenient when a so-called long diffusion wavelength condition is met, i.e., $(\gamma\delta G a)^2 \ll 1$. While double-PFG sequences are convenient, the disclosed methods can use other sequences that provide suitable diffusion encoding. The examples set forth below are representative, and should not be taken as limiting in scope. As defined herein, a double PFG sequence includes two gradient sequences that are substantially balanced either by applying gradients of differing polarities, or effectively inverting gradient encoded spins with an RF pulse (typically a 180 degree pulse) so that a second gradient pulse is effectively inverted. In some cases, portions of a first sequence and a second sequence overlap as shown in FIG. 1B.

As used in this application and in the claims, the singular forms "a," "an," and "the" include the plural forms unless the context clearly dictates otherwise. Additionally, the term "includes" means "comprises." Further, the term "coupled" means electrically or electromagnetically coupled or linked and does not exclude the presence of intermediate elements between the coupled items. The described systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like 'produce' and 'provide' to describe the disclosed methods. These terms are high-level abstractions of the actual operations that are performed. The actual operations that correspond to these terms will vary depending on the particular implementation and are readily discernible by one of ordinary skill in the art.

As used herein, the term 'signal' refers to time varying electromagnetic signals such as time varying electric fields, magnetic fields, voltages, currents, or other such time varying quantities. In addition, a 'recorded signal' is defined as a corresponding analog or digital record of such a time varying signal as for example, a set of stored digital data or other representations. Typically, time varying signals are sampled and the samples stored to form a recorded signal. For convenience, a quantity $q=\gamma\delta G/2\pi$ wherein $\gamma$ is a gyromagnetic ratio, $\delta$ is a duration of a magnetic field gradient pulse, and G is a magnitude of a pulsed magnetic field gradient is referred to herein as a magnetic resonance (MR) wavenumber. A quantity $q=\gamma\delta G/2\pi$ wherein G is a pulsed magnetic field gradient vector ($|G|=G$) is referred to herein as a magnetic resonance (MR) wavevector. In the following discussion, pulsed field gradients (PFGs) are generally assumed to include pulsed magnetic field gradients having a constant magnitude G for a time duration $\delta$. However, other filed gradients can be used, and this representation is selected for convenient discussion. Typically, a pulsed field gradient can be represented as having an effective magnitude $G_{eff}$ (or magnitude and direction) and an effective duration $\delta_{eff}$ so that analysis based on constant magnitude pulses can be informative.

For ease of explanation, additional pulses or pulse sequences used for purposes such as slice selecting in magnetic resonance imaging and fat suppression or saturation are not discussed herein. It will be appreciated that disclosed methods and apparatus can be configured for NMR based specimen evaluations or in conjunction with imaging or spatial localization. Finally, specimen compartments that exhibit restricted diffusion are referred to generically as pores herein, but such pores include a variety of structures in which spin diffusion is limited, and pores can have spherical, cylindrical, planar, ellipsoidal, oval, or other arbitrary shapes.

I. Double Pulsed Field Gradient Measurements with Arbitrary Timing

A. Free Diffusion

For convenient illustration of the disclosed methods, free (Gaussian) diffusion is considered first. The exact form of the signal attenuation obtained via arbitrary gradient waveforms is given by the expression:

$$E^{free} = \exp\left(-\gamma^2 D_0 \int_0^T dt \left|\int_0^t G(t')dt'\right|^2\right), \tag{1}$$

where $D_0$ is the bulk diffusivity and $G(t)$ is the effective time-dependent gradient waveform, which starts at $t=0$ and ends at $t=T$. Evaluating this expression for the effective pulse sequence of FIG. 1A, we obtain $$E_a^{free} = e^{-\gamma^2 D_0 \delta^2 (\Delta - \delta/3)(G_1^2 + G_2^2)}, \tag{2}$$

where $G_1=|G_1|$ and $G_2=|G_2|$. Similarly, for the experiment of FIG. 1B, we get $$E_b^{free} = e^{-\gamma^2 D_0 \delta^2 [(\Delta-\delta/3)(G_1^2+G_2^2)-(\delta/3)G_1G_2\cos\psi]}, \tag{3}$$

where $\psi$ is the angle between $G_1$ and $G_2$. The derivations of the signal attenuation expressions above is similar to the derivation of the well-known Stejskal-Tanner expression, which can be found in P. T. Callaghan, *Principles of Nuclear Magnetic Resonance Microscopy*, Clarendon Press, Oxford (1991), which is incorporated herein by reference. When either $G_1$ or $G_2$ is set to zero in the expressions for both experiments, the signal attenuation is given by the Stejskal-Tanner relation as expected.

B. Restricted Diffusion in Isotropic Pores

An expression, similar to Eq. 1 can be obtained that is valid for restricted diffusion taking place in D-dimensional isotropic pores with non-relaxing walls. The derivation is based on the realization that a matrix product approach an described in, for example, Callaghan, "A simple matrix formalism for spin echo analysis of restricted diffusion under generalized gradient waveforms," J. Magn. Reson. 129:74-84 (1997), originally designed to compute numerically the NMR signal attenuations obtained using generalized gradient waveforms, along with a discretization scheme described elsewhere herein, can be used as analytical tools. The details of this derivation can be found in Appendix A. Note that the geometries considered here are infinite parallel plates separated by a distance 2a, and cylinders and spheres of radius a for the cases of D=1, 2 and 3, respectively. Then the signal attenuation, for small values of $\gamma\delta Ga$, when the gradients are applied perpendicular to the restricting walls of the geometry, is given by $$E^{rest} \simeq 1 - 2\gamma^2 a^2 \sum_{n=1}^{\infty} s_{Dn} \int_0^T dt\, e^{\omega_{Dn} t} G(t) \cdot F_{Dn}(t), \tag{4}$$

with the following definitions:

$$F_{Dn}(t) = \int_t^T G(t') e^{-\omega_{Dn} t'} dt', \tag{5}$$

$$s_{Dn} = \frac{1}{\alpha_{Dn}^2(\alpha_{Dn}^2 - D + 1)}, \tag{6}$$

where $s_{Dn}$ satisfy the relationship $$\sum_{n=1}^{\infty} s_{Dn} = \frac{1}{2(2+D)}, \tag{7}$$

and finally $$\omega_{Dn} = \frac{\alpha_{Dn}^2 D_0}{a^2}, \tag{8}$$

where $\alpha_{1n}=(n-\frac{1}{2})\pi$, and $\alpha_{2n}$ and $\alpha_{3n}$ are, respectively, the roots of the derivatives of the first order Bessel and spherical Bessel functions, i.e., they satisfy the expressions $J_1'(\alpha_{2n})=0$ and $j_1'(\alpha_{3n})=0$. The subscripts D will be dropped henceforth for brevity and it should be noted that these subscripts are not intended to signify a diffusion coefficient.

Evaluating Eq. 4 for the effective gradient waveforms of FIGS. 1A-1B, we obtain $$E_a^{rest} \cong 1 - (A(G_1^2+G_2^2) + B\, G_1 G_2 \cos\psi), \tag{9}$$

and $$E_b^{rest} \cong 1 - (A(G_1^2+G_2^2) + B'\, G_1 G_2 \cos\psi), \tag{10}$$

with the definitions:

$$A = 2\gamma^2 a^2 \sum_{n=1}^{\infty} s_n \left[ \frac{2\delta}{\omega_n} - \frac{1}{\omega_n^2} \left( \begin{array}{c} 2 - 2e^{-\omega_n \delta} + e^{-\omega_n(\Delta-\delta)} - \\ 2e^{-\omega_n \Delta} + e^{-\omega_n(\Delta+\delta)} \end{array} \right) \right], \quad (11)$$

$$B = 2\gamma^2 a^2 \sum_{n=1}^{\infty} \frac{s_n}{\omega_n^2} \left( \begin{array}{c} e^{-\omega_n(t_m-\delta)} - 2e^{-\omega_n t_m} + e^{-\omega_n(t_m+\delta)} - \\ 2e^{-\omega_n(\Delta+t_m-\delta)} + 4e^{-\omega_n(\Delta+t_m)} - \\ 2e^{-\omega_n(\Delta+t_m+\delta)} + e^{-\omega_n(2\Delta+t_m-\delta)} - \\ 2e^{-\omega_n(2\Delta+t_m)} + e^{-\omega_n(2\Delta+t_m+\delta)} \end{array} \right), \quad (12)$$

and $$B' = 2\gamma^2 a^2 \sum_{n=1}^{\infty} s_n \times \left[ \frac{2\delta}{\omega_n} - \frac{1}{\omega_n^2} \left( \begin{array}{c} 2 - 2e^{-\omega_n \delta} + 2e^{-\omega_n(\Delta-\delta)} - \\ 4e^{-\omega_n \Delta} + 2e^{-\omega_n(\Delta+\delta)} - \\ e^{-\omega_n(2\Delta-\delta)} + 2e^{-\omega_n 2\Delta} - \\ e^{-\omega_n(2\Delta+\delta)} \end{array} \right) \right] \quad (13)$$

Comparing the signal attenuation expressions for free diffusion with those for restricted diffusion suggests several interesting distinctions. In the case of free diffusion, the signal attenuation is independent of the mixing time, which is not the case when restrictions are present. Second, the free diffusion signal decay for the pulse sequence of FIG. 1B suggests that the signal intensity depends on the angle between the gradient vectors, whereas the first pulse sequence leads to a signal decay, which is independent of the gradient directions. However, the angular dependence of the pulse sequence of FIG. 1B, in the case of free diffusion, is merely an effect of the finite pulse duration, and as such it is not a fundamental feature of the double-PFG experiment in the case of free diffusion. This peculiar behavior Is essentially due to the way "cross terms" play out when the two pulses overlap. Although it can be neglected when the $\delta \ll \Delta$ condition is met, it is significant when $\delta$ is close to $\Delta$. For example, when $\delta=\Delta$, and taking $|G_1|=|G_2|$, the logarithm of the signal attenuation is proportional to $4-\cos \psi$. Note that the restricted diffusion signal decay has a similar angular dependence (though in the opposite sense) in both pulse sequences. Consequently, we will now consider only the pulse sequence illustrated in FIG. 1A. In this case, an angular dependence of the signal intensity becomes a characteristic feature of restricted diffusion and in turn makes it possible to distinguish restricted diffusion from Gaussian diffusion by varying only the angle between the two gradient vectors.

We note that the same pulse sequence would lead to $\psi$-independent signal decays when the diffusion process is multi-Gaussian, which would occur when there are two distinct Gaussian compartments. Both restricted diffusion and multi-Gaussian processes may lead to similar echo attenuations when single-PFG experiments are performed.

Figures 2A, 2B:
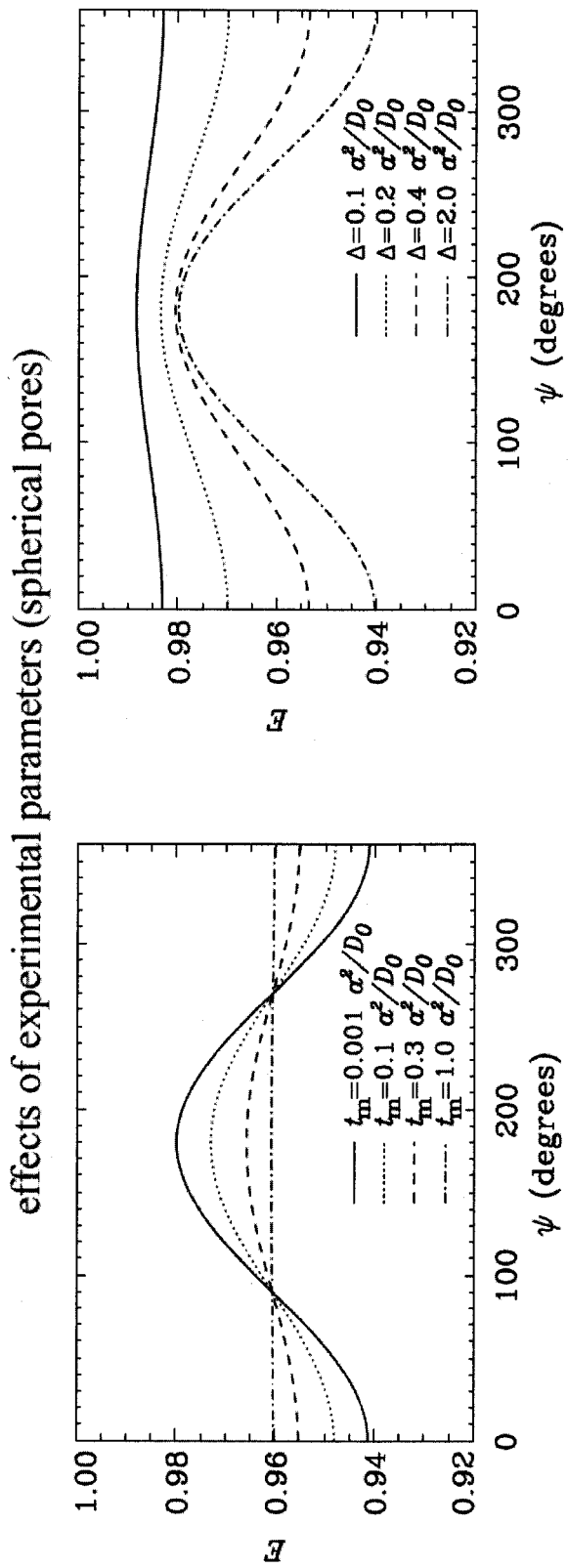
FIGS. 2A-2D illustrate dependence of the NMR signal intensity from spherical pores on the angle between the gradients used in the two encoding blocks of a double-PFG experiment. The parameters used in the simulations were: (a) $(\gamma\delta G_1 a)^2=(\gamma\delta G_2 a)^2=0.1$, $\delta=0.001$ $a^2/D_0$, $\Delta=a^2/D_0$; (b) $(\gamma\delta G_1 a)^2=(\gamma\delta G_2 a)^2=0.1$, $\delta=0.001$ $a^2/D_0$, $t_m=0.002$ $a^2/D_0$; (c) $(\gamma\delta G_1 a)^2=(\gamma\delta G_2 a)^2=0.1$, $\Delta=a^2/D_0$, $t_m=0.002$ $a^2/D_0$; (d) $\delta=0.001$ $a^2/D_0$, $\Delta=a^2/D_0$, $t_m=0.002$ $a^2/D_0$.
Figure 2C:
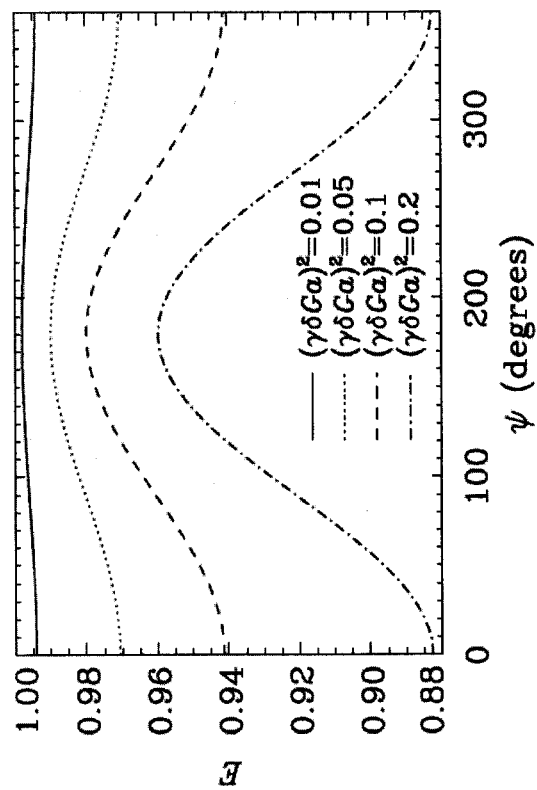
Figure 2D:
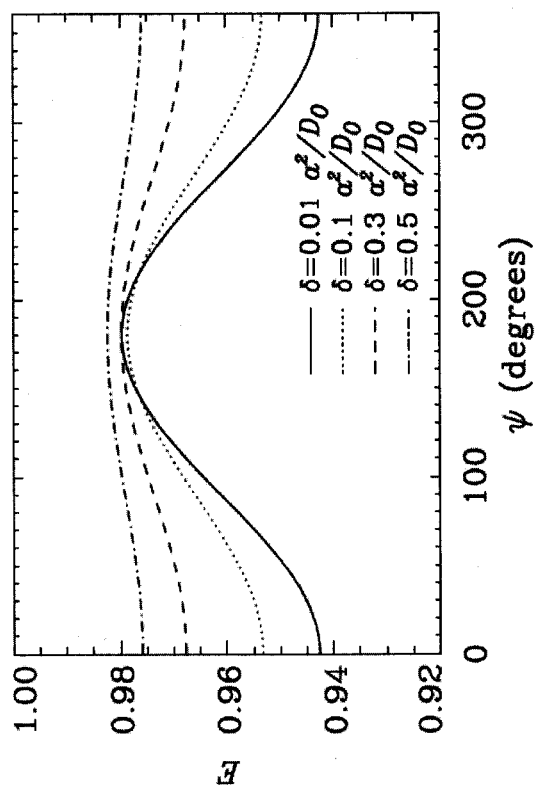

FIGS. 2A-2D show the dependence of the signal from spherical pores on the angle between $G_1$ and $G_2$. As can be seen in FIG. 2A, there is significant angular variation of the signal at short mixing times. This apparent anisotropy is a manifestation of the influence of the pore boundaries on the diffusing molecules, which becomes observable at short mixing times, i.e., when there is significant correlation in the movements of spins during the separate encoding periods. Panel (b) of the same figure illustrates the signal intensity with varying $\Delta$-values. It is clear that the angular dependence tends to disappear as $\Delta$ gets shorter. However, for small pores, i.e., when a is small, the long $\Delta$ requirement is easy to fulfill. Similar behavior is observed when the diffusion gradient pulse width ($\delta$) gets longer as demonstrated in FIG. 2C. Note that since we are primarily interested in the long wavelength behavior, i.e., the case of small $\gamma\delta Ga$, applying relatively short pulses is likely to be feasible. Finally, in FIG. 2D, we illustrate the angular variation in the NMR signal with different values for the gradient strength. From a theoretical point of view, smaller gradients are preferred to fulfill the $(\gamma\delta Ga)^2 \ll 1$ condition, violation of which could make the higher order terms significant, potentially leading to a bias in the pore size estimates. However, FIG. 2D suggests that larger gradients will lead to sharper signal profiles. This is particularly desirable for accurate resolution of the angular variation when the signal-to-noise ratio (SNR) is limited. Therefore, an optimal value for the gradient strength—which will depend on the SNR as well as the pore size—should exist.

Figure 3A:
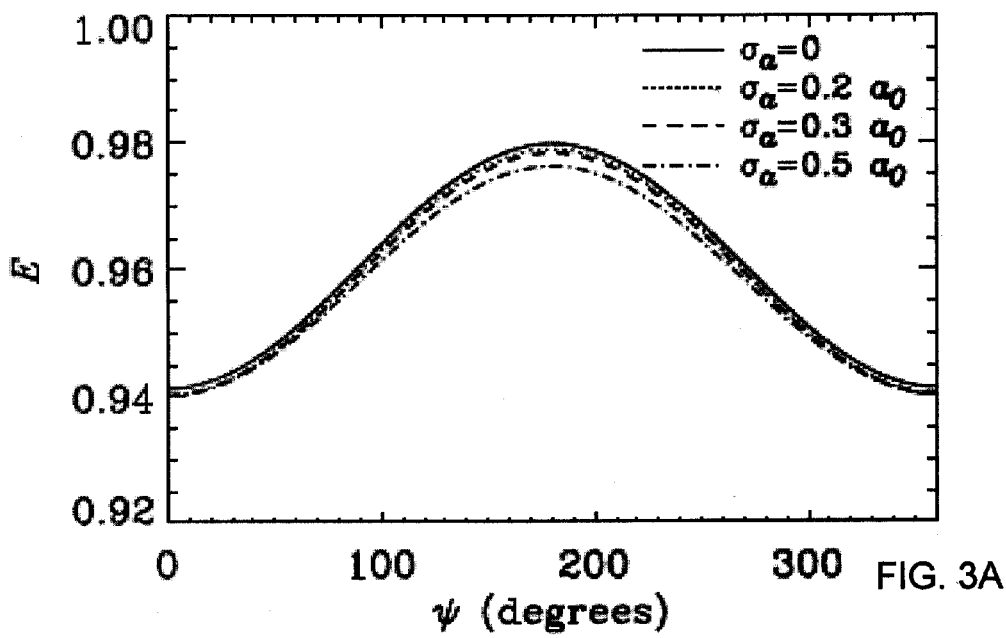
FIGS. 3A-3B illustrate additional simulated NMR signal intensities. In all simulations $(\gamma\delta G_1 a)^2=(\gamma\delta G_2 a)^2=0.1$, $t_m=0.002$ $a^2/D_0$, $\Delta=a^2/D_0$, $\delta=0.001$ $a^2/D_0$.

In FIG. 3A the effects of variations in pore size within the specimen are provided by averaging the signal attenuations from 10,000 spheres whose radii are distributed according to a Rician distribution whose resulting mean and standard deviation values are denoted by $a_0$ and $\sigma_a$, respectively. Here, a Rician distribution is used to ensure that the radii will be positive even for relatively large values of $\sigma_a$. For each level of polydispersity, characterized by the $\sigma_a$ value, an apparent estimated pore size can be obtained by fitting the signal values to the theoretical expression. In one example fitting, the percentage errors were 0.00, 0.72, 1.6, and 2.5 for the cases of $\sigma_a=0$, $\sigma_a=0.2a$, $\sigma_a 32\ 0.3a$, and $\sigma_a=0.5a$, respectively. Thus, this method is robust to the heterogeneity of the specimen, making it possible to estimate an average pore size meaningfully by using double-PFG experiments.

Figure 3B:
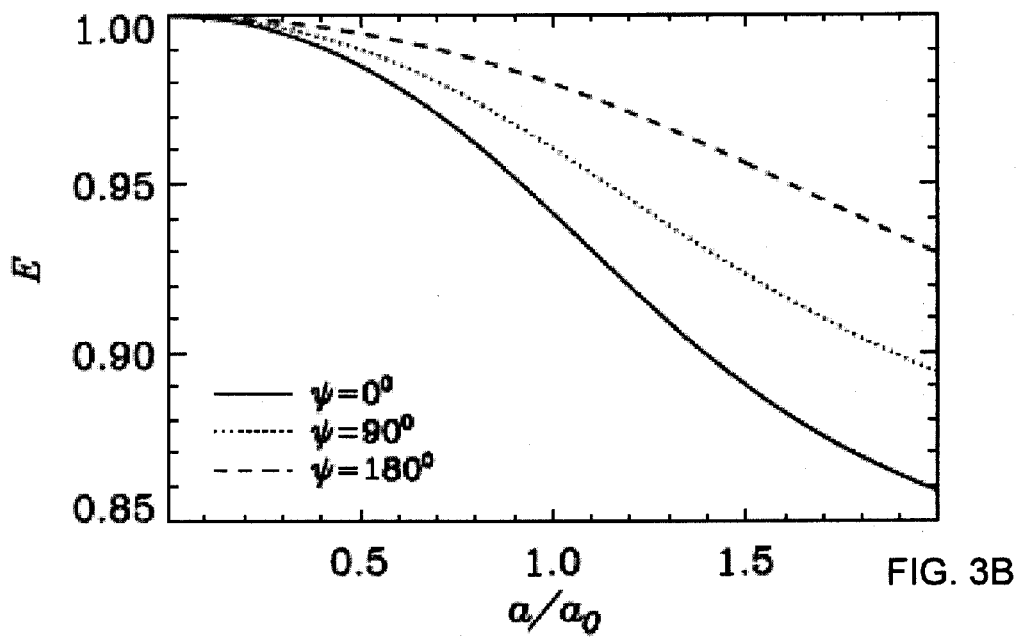

To understand the robustness of the signal on polydispersity, in FIG. 3B we plot the signal for three values of $\psi$ as a function of the pore size. Clearly, around the mean value of $a_0$, the signal curves are linear although some nonlinearity is visible when the gradients are in the opposite direction. Therefore, a pore size distribution, symmetric around the mean, with reasonably small standard deviations can be expected to yield accurate estimates of the average pore size as the effects of larger pores would be canceled by those due to small pores. However, most distributions of interest, like the Rician distributions we employed, are non-symmetric. Therefore, the exact nature of the deviations in the pore size estimates from the mean pore size depends on the particular distribution as well as the dependence of the signal on pore size.

C. Diffusion in Anisotropic Pores

Results for isotropic pores are provided above, and anisotropic environments can also be modeled using the same framework. For simplicity, specimens of coherently packed, infinitely long cylinders oriented along the direction u are considered. Then the gradient vectors $G_1$ and $G_2$ can be decomposed into components parallel and perpendicular to u. This enables the evaluation of the signal intensity as a product of the signal attenuations from free diffusion and restricted diffusion with D=2:

$$E_a^{cyl}(u) = E_a^{free}(g_1, g_2) \times E_a^{rest}(G_1 - g_1 u, G_2 - g_2 u), \quad (14)$$

where $g_i = G_i \cdot u$. The echo attenuation at long wavelengths is given by $$E_a^{cyl}(u) \simeq e^{-\gamma^2 D_0 \delta^2 (\Delta - \delta/3)(g_1^2 + g_2^2)} \times (C + A g_1^2 + A g_2^2 + B g_1 g_2), \quad (15)$$

where $$C = 1 - A(G_1^2 + G_2^2) - B G_1 G_2 \cos \psi. \quad (16)$$

Figure 4B:
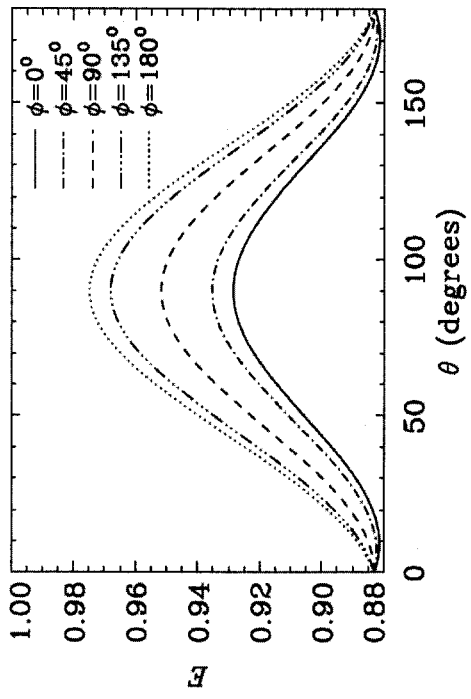
FIGS. 4A-4D illustrate additional simulated NMR signal intensities. In all simulations the following parameters were used: $\delta=0.001$ $a^2/D_0$, $\Delta=a^2/D_0$, $t_m=0.002$ $a^2/D_0$, and $(\gamma\delta G_1 a)^2=(\gamma\delta G_2 a)^2=0.1$.
Figure 4A:
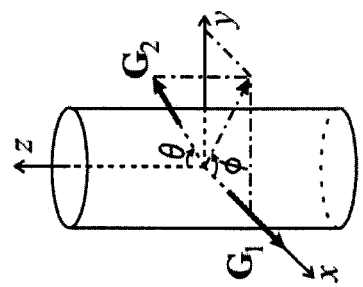

FIG. 4B shows the simulated signal attenuation when one of the gradients is applied along the direction perpendicular to the cylinder's surface as a function of the orientation of the second gradient. The geometry and gradient orientations are illustrated in FIG. 4A. The θ dependence of each curve, when φ=90°, is indicative of the ensemble anisotropy due to the coherence in the cylinders' orientations. The fact that different curves corresponding to different azimuthal angles (φ) do not coincide at θ=90° is a consequence of the microscopic anisotropy induced by restricted diffusion. Therefore, using double-PFG experiments, it is possible to probe ensemble (i.e., global) and microscopic anisotropy simultaneously. Note that while the orientation of the cylinders can be estimated using simple models like a diffusion tensor description of the quadratic term of the signal attenuation in a single-PFG experiment, such a model would not account for restricted diffusion, making it impossible to estimate the diameters of the cylinders at long wavelengths.

1. Ensemble Anisotropy

The case of variability in the cylinders' orientations is provided in this section. A general orientation distribution function, $f(u)$, can be defined in terms of a Laplace series, i.e., $$f(u) = \sum_{l=0,2,4,...}^{\infty} \sum_{m=-l}^{l} f_{lm} Y_{lm}(u), \quad (17)$$

where $Y_{lm}(u)$ are spherical harmonics. The resulting NMR signal attenuation is given by $$E_a^{cyl}(f(u)) = \sum_{l=0,2,4,...}^{\infty} \sum_{m=-l}^{l} f_{lm} \times (CI_{lm}^{0,0} + AI_{lm}^{2,0} + AI_{lm}^{0,2} + BI_{lm}^{1,1}), \quad (18)$$

where $I_{lm}^{p,q}$ is given by the following integral over the sphere:

$$I_{lm}^{p,q} = \int_S du Y_{lm}(u) g_1^p g_2^q e^{-\gamma^2 D_0 \delta^2 (\Delta - \delta/3)(g_1^2 + g_2^2)}. \quad (19)$$

Although the analytic evaluation of this integral is possible, it is quite tedious and the result involves many sums and Wigner matrices. Consequently, in our implementation, we adopted a numerical scheme and employed an iterated Gaussian quadrature algorithm with 96 transformation points.

Figure 4D:
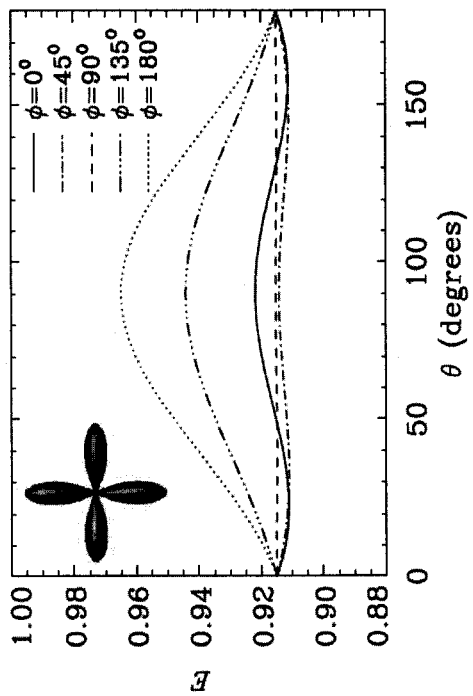
Figure 4C:
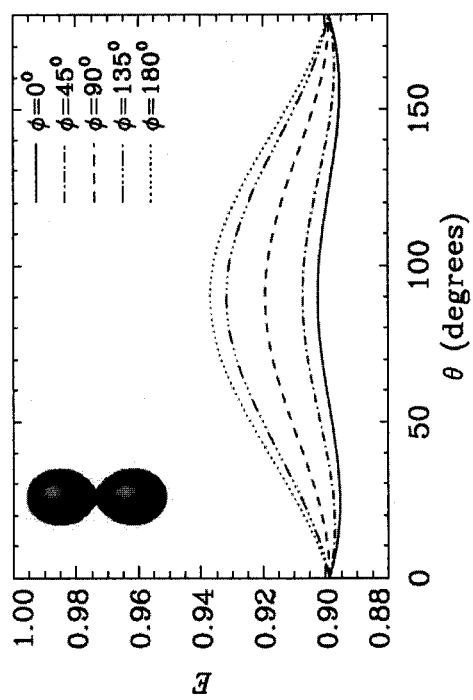

FIG. 4C shows the NMR signal attenuation when the cylinders have an angular dispersion, where the associated orientation distribution function is characterized by a second order Cartesian tensor whose largest eigenvalue is 10 times its other two eigenvalues. The corresponding $f_{lm}$ coefficients were computed using the relationships provided in Ozarslan and Mareci, Magn. Res. Med. 50:955 (2003). The principal eigenvector, i.e., the average orientation of the cylinders, was oriented along the z-axis. Note that the simulations of FIG. 4B are just a special case of ensemble anisotropy when the orientation distribution function is a delta-function. A comparison of FIGS. 4B and 4C shows that the angular dispersion of the cylinders leads to a substantial suppression of ensemble anisotropy as demonstrated by the flattening of the θ-dependence. The φ-dependence, however, is affected less significantly.

In FIG. 4D, we show simulation results from a bimodal orientation distribution function. This distribution was generated from an $8^{th}$-order spherical tensor whose components, determined using the techniques in Ozarslan et al., NeuroImage 1:1086 (2006), will not be included for brevity. As the inset in FIG. 4D shows, two bundles of cylinders were used, whose average orientations are along the y and z axes, respectively. Note that the curves are qualitatively different from those of panels (b) and (c), suggesting the possibility of the resolution of fiber crossings using double-PFG experiments at long diffusion wavelengths.

Notably, when φ is equal to 90°, i.e., when $G_2$ spans the plane of the distinct mean fiber orientations, the θ-dependence of the signal almost disappears. To understand this insensitivity on θ when φ=90°, we consider the case of two coherent and equally populated bundles, which are oriented along the y and z axes, respectively. Further assuming that $\gamma^2 D_0 \delta^2 (\Delta - \delta/3) G_2^2 \ll 1$, a straightforward application of Eq. 15 yields the expression $$E \simeq 1 - A G_1^2 - (A + \gamma^2 D_0 \delta^2 (\Delta - \delta/3)) \frac{G_2^2}{2} \quad (20)$$

for the signal attenuation, which is independent of θ. The very slight variation of the signal observed in FIG. 4D at φ=90° is due to the orientational incoherence within the individual bundles. Note that the above expression is valid only when the two fiber bundles are perpendicular to each other.

2. Isotropically Distributed Pores: A Special Case and a 'Component' of General Distributions Finally, results corresponding to all the isotropically distributed fibers are presented, which can be seen as a special case of the treatment of the previous subsection. However, because an irreducible representation of the orientation distribution function is employed, it can also be envisioned as the "isotropic component" of a possibly anisotropic orientation distribution. Therefore, the anisotropy predicted here can be attributed only to microscopic anisotropy even in the presence of ensemble anisotropy.

Note that regardless of the orientation distribution function, the first component of the spherical tensor representing it is given by $f_{00} = (4\pi)^{-1/2}$, which is a consequence of the normalization condition. In fact, this is the only nonzero coefficient when isotropic distributions are concerned. Therefore, the NMR signal attenuation is given by $$E_a^{iso}(f(u)) = \frac{1}{\sqrt{4\pi}} (CI_{00}^{0,0} + AI_{00}^{2,0} + AI_{00}^{0,2} + BI_{00}^{1,1}). \quad (21)$$

Since the integrand in the definition of $I_{00}^{p,q}$ is given in terms of dot products, it is rotationally invariant. Therefore, without loss of generality, the gradient vectors can be taken to be $G_1^T = G_1(1,0,0)$ and $G_2^T = G_2(\cos\psi, \sin\psi, 0)$. This makes the evaluation of $I_{00}^{p,q}$ simple, which is given by $$I_{00}^{p,q} = \sqrt{4\pi} \sum_{k=0}^{\infty} \sum_{r=0}^{k} \frac{(-\gamma^2 D_0 \delta^2 (\Delta - \delta/3))^k}{(k-r)! r!} \quad (22)$$

$$\frac{(2r+q)!}{(2k+p+q+1)!!} G_1^{2k-2r+p} G_2^{2r+q} \times$$

$$\sum_{j=0,2,4,...}^{2r+q} \frac{(j-1)!!(2k+p+q-j-1)!!}{j!(2r+q-j)!} (\cos^{2r+q-j}\psi)(\sin^j\psi).$$

Figure 5A:
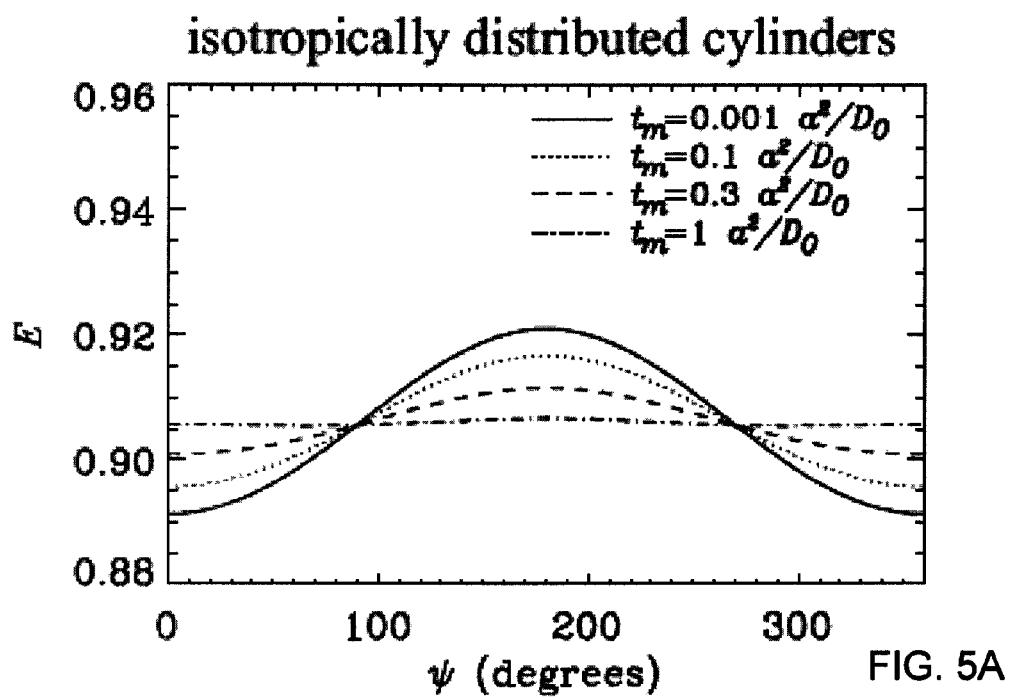
FIGS. 5A-5B illustrate NMR signal attenuation from cylinders isotropically distributed in space, obtained using simulated double-PFG experiments. In both simulations, the following parameters were used: $(\gamma\delta G_1 a)^2=(\gamma\delta G_2 a)^2=0.1$, $\delta=0.001$ $a^2/D_0$.

FIG. 5A shows the NMR signal attenuation from isotropically distributed cylinders. As pointed out above, only one mechanism of anisotropy influences the quadratic term, i.e., anisotropy due to microscopic restrictions. The angular variation of the signal is less than that predicted for coherently oriented cylinders. It is also meaningful to compare these plots with FIG. 2A, which shows the signal intensity with identical experimental parameters from spherical pores—another specimen that possesses only microscopic anisotropy. Qualitatively, the behavior is identical. However, because the molecules within isotropically distributed cylinders are not fully restricted, they suffer more signal loss.

3. Angular Signal Profile at Very Long Diffusion Times

Figure 5B:
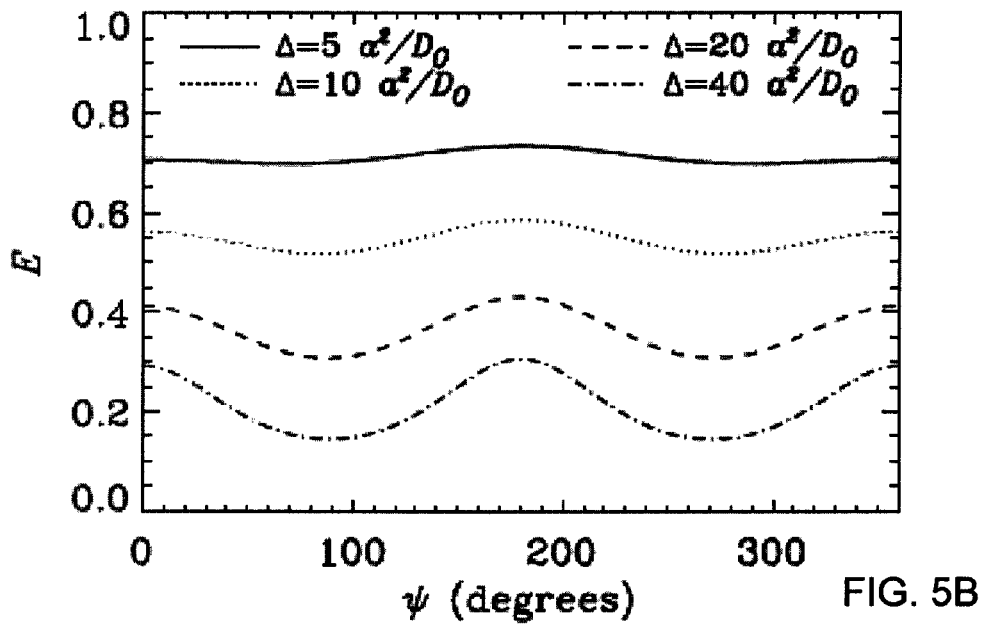
Figure 6:
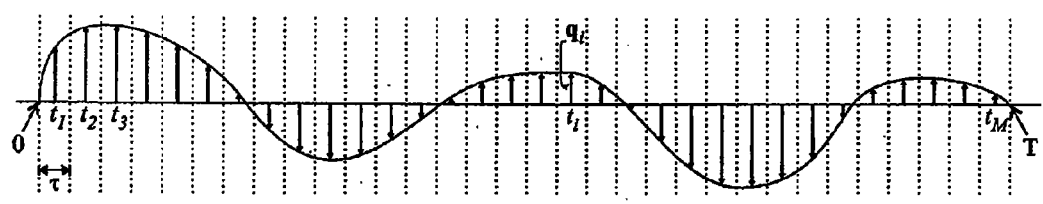
FIG. 6 illustrates a general NMR waveform. The continuous line depicts the general NMR gradient waveform and an approximation is achieved by dividing the time axis into M intervals each of which contains an impulse. Note that the above waveform depicts the effective gradients, i.e., it is formed by taking into account the possible application of radiofrequency pulses.
Figure 7D:
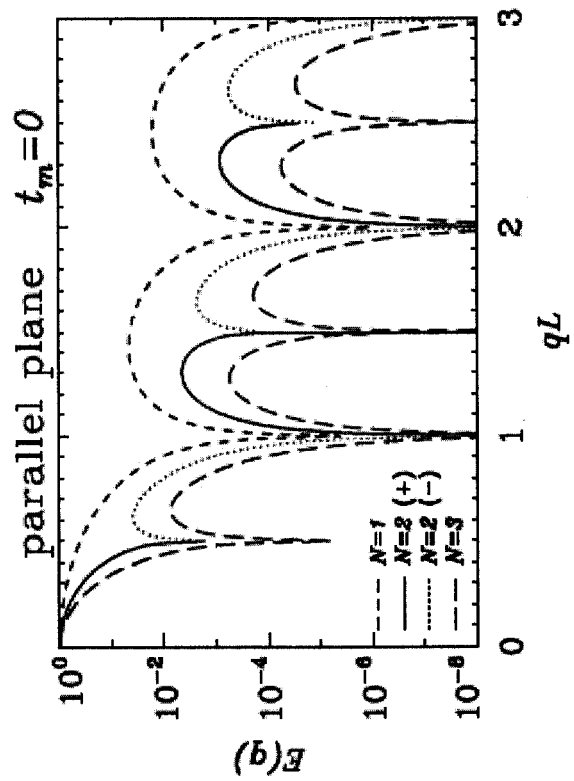
FIGS. 7A-7F illustrate signal attenuation as a function of q with varying number of diffusion gradient pairs for parallel plane pore with spacing L (top), cylindrical pore with radius r (middle) and spherical pore with radius R (bottom). The left column shows the results obtained in the limit $t_m \to \infty$ whereas $t_m=0$ case was shown on the right column. In both cases $\delta=0$ and $\Delta \to \infty$. The continuous and dotted lines both illustrate the curve obtained with N=2 where the former shows the positive sections and the latter shows the negative sections after flipping.
Figure 7A:
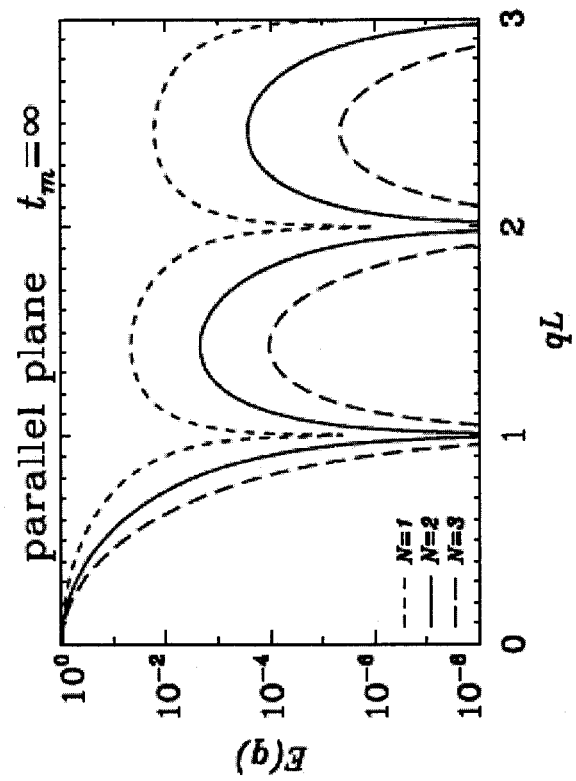
Figure 7E:
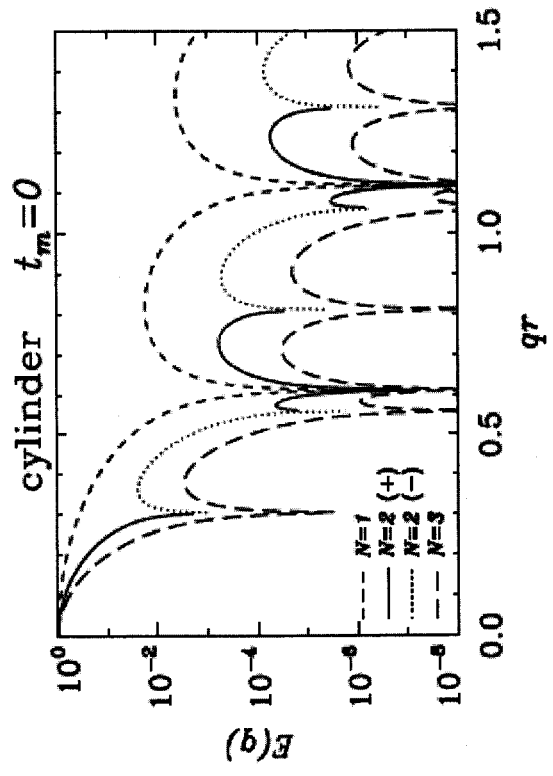
Figure 7B:
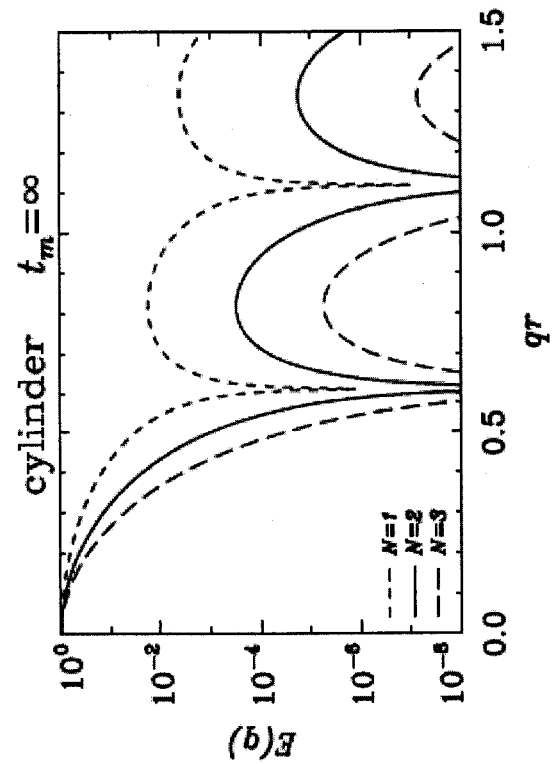
Figure 7F:
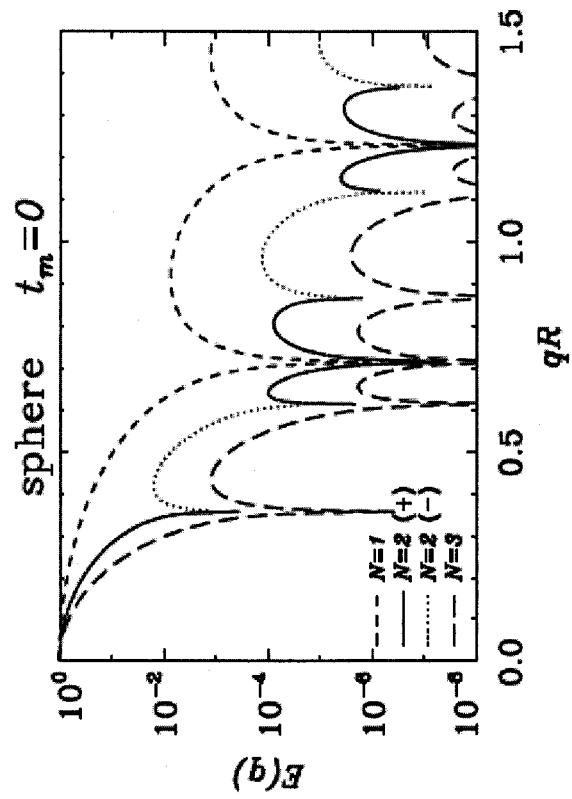
Figure 7C:
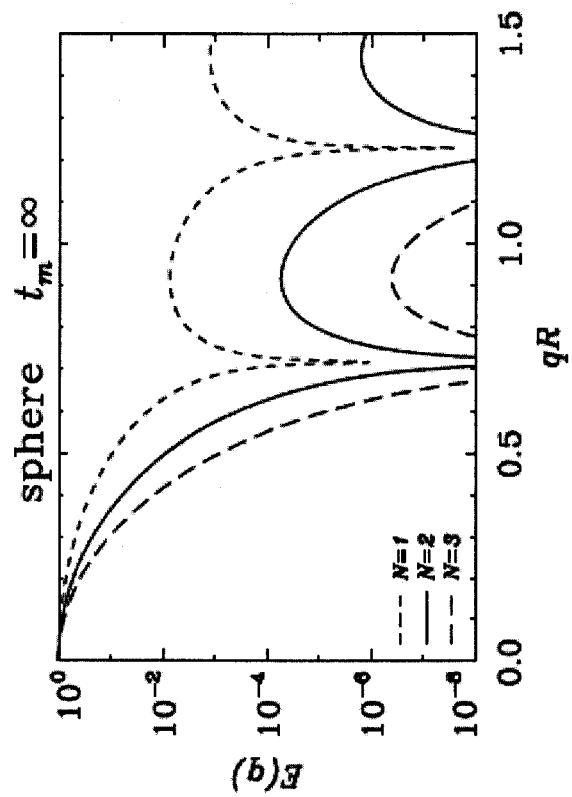
Figure 8D:
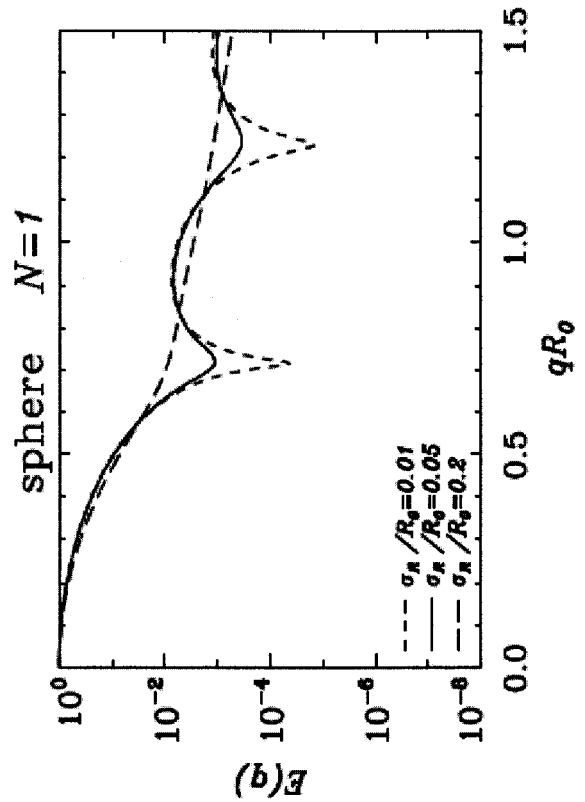
FIGS. 8A-8F illustrate signal attenuation as a function of q from distributions of parallel planes (left column) and spheres (right column). The mean and standard deviation of the spacings of the parallel planes are denoted by $L_0$ and $\sigma_L$ whereas the mean and standard deviations of the radii of the spheres are denoted by $R_0$ and $\sigma_R$ respectively. Simulations of experiments with number of pulse pairs varying 1 through 3 (top to bottom) are shown, $\delta=t_m=0$, $\Delta \to \infty$.
Figure 8A:
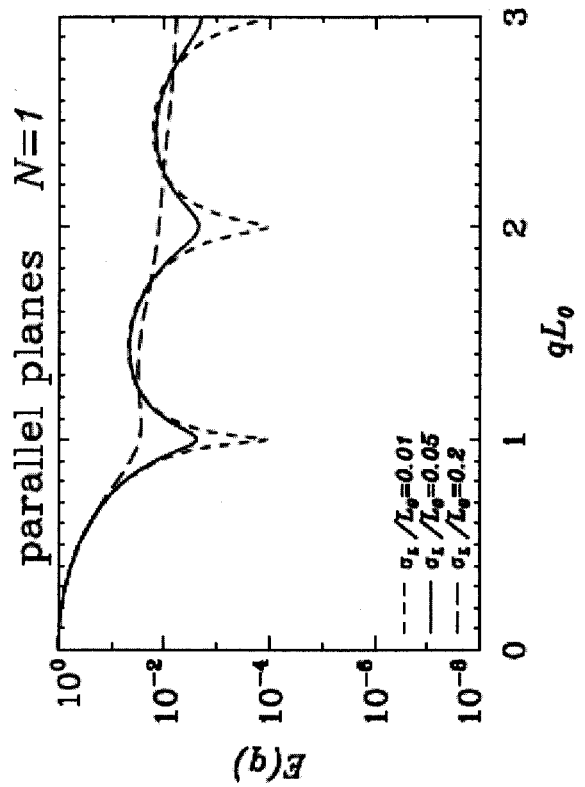
Figures 8B, 8E:
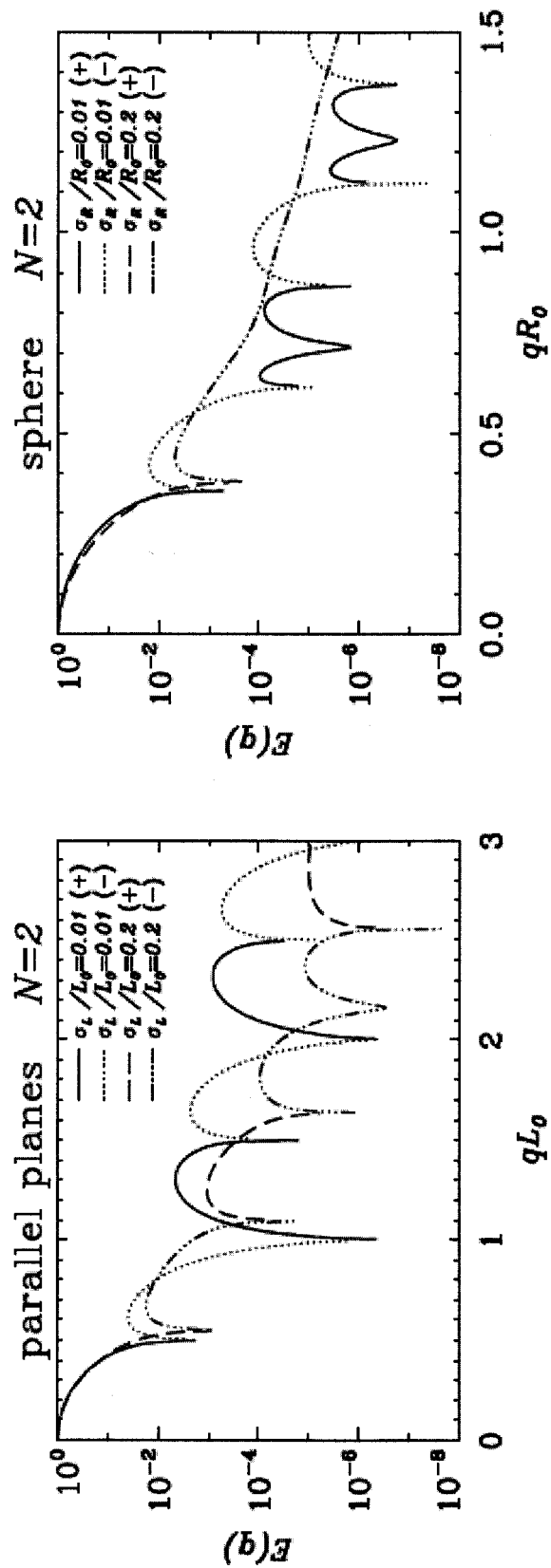
Figure 8F:
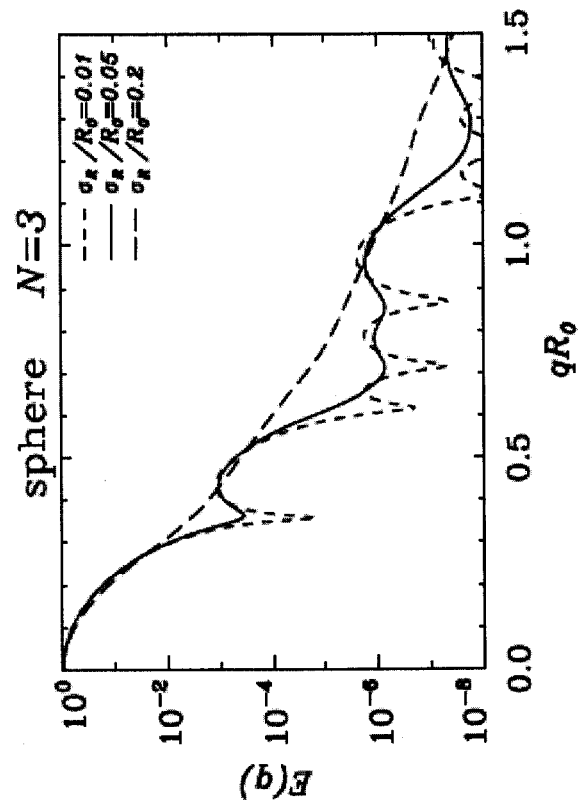
Figure 8C:
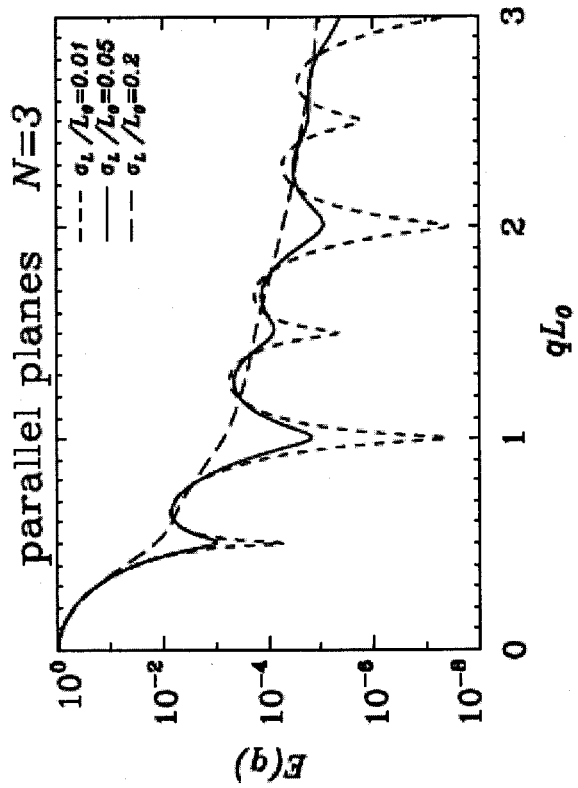
Figure 9D:
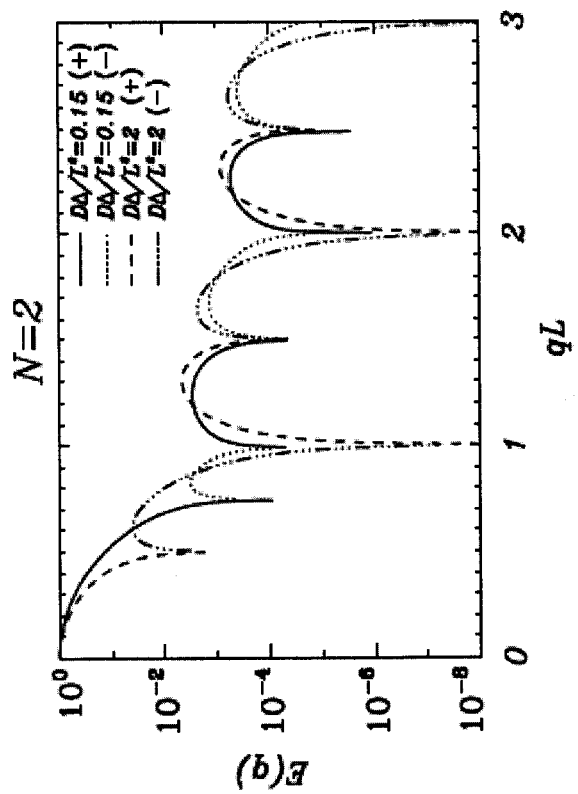
FIGS. 9A-9F illustrate signal attenuation as a function of q with varying values of $\Delta$ for the parallel plane pore. Each figure depicts the signal attenuation curve with a different number of diffusion gradient pulse pairs. $\delta=0$, $t_m=0$.
Figure 9A:
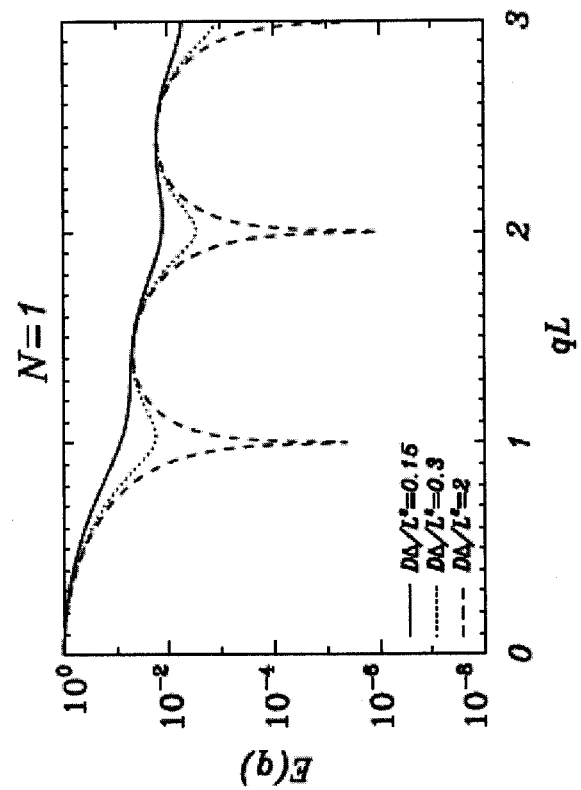
Figure 9E:
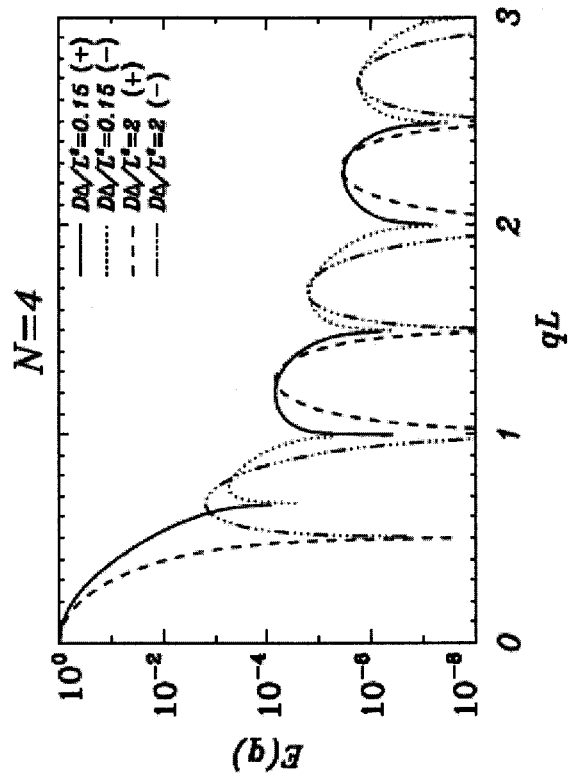
Figure 9B:
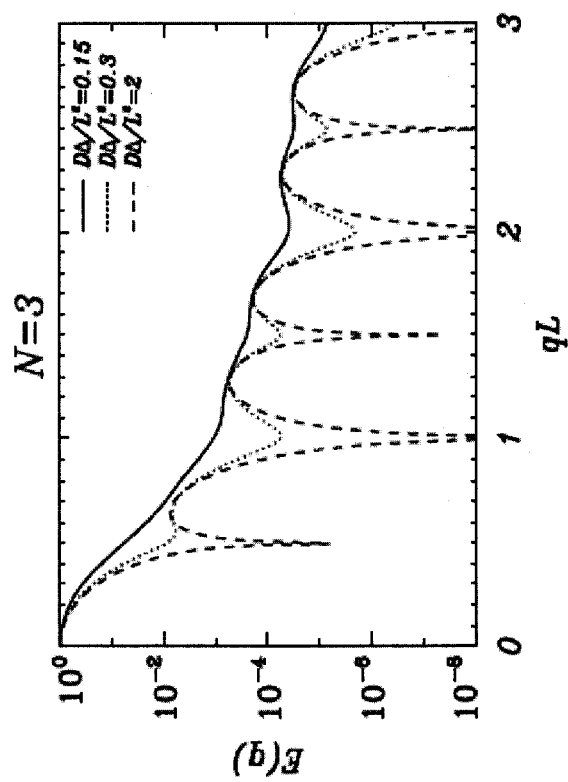
Figure 9F:
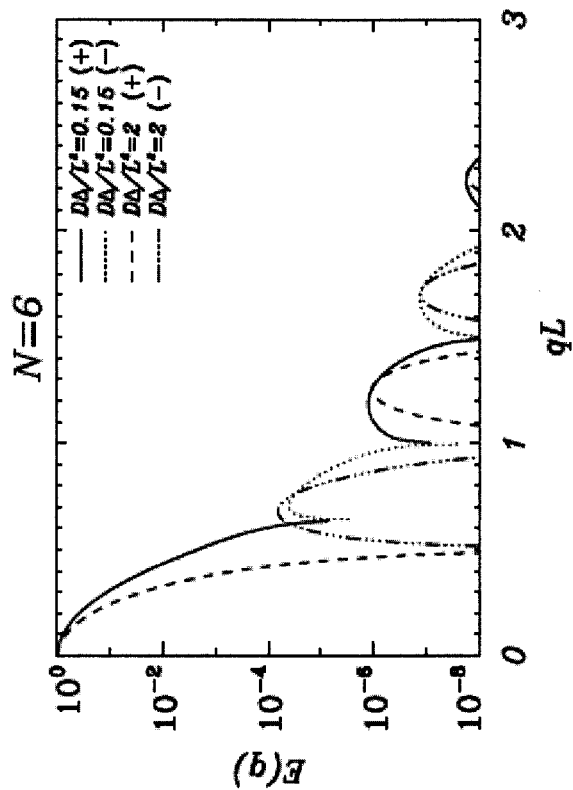
Figure 9C:
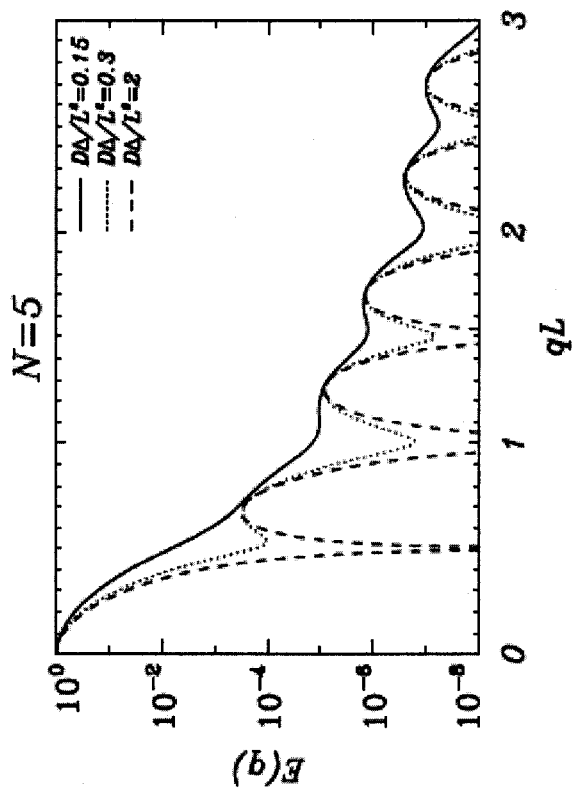

Unlike the case of spherical pores, the loss of signal from isotropically distributed cylinders can be enhanced significantly by increasing the diffusion time. As depicted in FIG. 5B, at very long diffusion times, the signal when the two gradients are approximately parallel decreases less and eventually approaches the case of antiparallel gradients—consistent with the case of infinitesimally small a.

In this section, we will elaborate on this qualitatively different angular dependence predicted for very large values of $\Delta$. For this purpose, we consider a special yet instructive case of the experiment, where the following conditions are met: $t_m = \delta \to 0$, $G = G_1 = G_2$, $T_0 = D_0\Delta/a^2 \gg 1$, $\kappa = \gamma\delta Ga \ll 1$, and define the dimensionless constant $\zeta = \gamma^2\delta^2G^2D_0\Delta = \kappa^2 T_0$. Note that $\zeta$ can assume any value as it is the product of a small quantity ($\kappa^2$) and a large quantity ($T_0$). In fact, our goal in this section is to describe the behavior of the angular signal profile when one moves from the $\zeta \leq 1$ to $\zeta \gg 1$ regime.

When the above conditions are met, the attenuations due to restricted and free diffusion are given by the relations $$E_a^{rest}(u) = 1 - \frac{\gamma^2\delta^2 a^2}{4}(|G_{1\perp}|^2 + |G_{2\perp}|^2 + G_{1\perp} \cdot G_{2\perp}) \quad (23a)$$

$$E_a^{free}(u) = e^{-\gamma^2\delta^2 D_0\Delta(g_1^2 + g_2^2)}, \quad (23b)$$

where $G_{i\perp} = G_i - g_i u$ is the component of the i-th gradient (i=1, 2) perpendicular to the cylinder's axis. Note that in the above expressions we are considering the signal from a single tube whose axis is specified by the unit vector u whose polar and azimuthal coordinates will be denoted by $\theta$ and $\phi$, respectively.

We first consider the cases $\psi=0$ and $\psi=\pi$. Because the dot products of $G_1$ with $G_2$ are given by $+G^2$ and $-G^2$, we will refer to these two cases by the superscripts "+" and "−", respectively. Since the cylinders are isotropically distributed, without loss of generality, the first diffusion gradient can be taken to be along the z-direction, i.e., $G_1 = Gz$. Then $G_2^\pm = \pm Gz$. It is straightforward to show that $g_1 = \pm g_2^\pm = G\cos\theta$, $G_{1\perp} = \pm G_{2\perp}^\pm$, and $|G_{1\perp}| = |G_{2\perp}^\pm| = G\sin\theta$. These lead to a simple expression for the signal attenuation from a single cylinder, given by $$E_a^\pm(\theta, \phi) = e^{-2\zeta\cos^2\theta}\left(1 - \frac{\xi^\pm\kappa^2}{4}\sin^2\theta\right), \quad (24)$$

where $\xi^+=3$, and $\xi^-=1$. Averaging over all cylinder orientations yields $$E_a^\pm = \int_0^1 e^{-2\zeta\mu^2}\left[1 - \frac{\xi^\pm\kappa^2}{4}(1-\mu^2)\right]d\mu. \quad (25)$$

Next, we consider the case of if $\psi=90°$, which will be denoted by the superscript "⊥". Similar to the cases in the preceding paragraph, without loss of generality, we can take the two gradient vectors to be $G_1 = Gx$ and $G_2 = Gy$. It can be shown that $g_1 = G\sin\theta\cos\phi$, $g_2 = G\sin\theta\sin\phi$, $|G_{1\perp}|^2 = G^2(1-\sin^2\theta\cos^2\phi)$, $|G_{2\perp}|^2 = G^2(1-\sin^2\theta\sin^2\phi)$ and $G_{1\perp}\cdot G_{2\perp} = -G^2\sin^2\theta\sin\phi\cos\phi$. Using Eqs. 23a and b, the signal attenuation from a single tube is given by $$E_a^\perp(\theta, \phi) = e^{-\zeta\sin^2\theta}\left[1 - \frac{\kappa^2}{4}(2 - \sin^2\theta(1 + \sin\phi\cos\phi))\right]. \quad (26)$$

This equation can be integrated over the sphere to yield $$E_a^\perp = \int_0^1 e^{-\zeta(1-\mu^2)}\left[1 - \frac{\kappa^2}{4}(1 + \mu^2)\right]d\mu. \quad (27)$$

Although Eqs. 26-27 can be evaluated analytically, the results are not included as we can infer the desired information directly from these equations. Note that in these equations, the exponential terms are due to free diffusion along the tubes' orientations while the factors in square brackets are due to restricted diffusion. Because of the $\kappa^2 \ll 1$ condition, the effect of restricted diffusion on the differences between the resulting signal attenuations corresponding to the three different $\psi$-values considered is limited. When the diffusion time is not very long so that $\zeta$ is small, the effect of free diffusion can be neglected. However, as $\zeta$ is increased, the differences due to free diffusion attenuation become more and more significant, eventually making the differences due to terms in square brackets negligible. Since the free diffusion expressions are identical in the $\psi=0$ and $\psi=180°$ cases, as the value of $\zeta$ is increased, we start seeing similar values for $E_a^+$ and $E_a^-$. However, note that the free diffusion factor in Eq. 27 is different from the one in Eq. 25, giving rise to the more rapid collapse of the signal as $\zeta$ is increased at $\psi=90°$.

Thus, when the diffusion time is very long so that $\zeta$ is large, those cylinders whose orientation vectors have a significant component along either of the two diffusion gradients do not contribute to the aggregate signal significantly. Since more of the tubes will be in this situation when $\psi=90°$, the corresponding signal is lower than the signal at $\psi=0°$ or $\psi=180°$.

D. Discussion

The form of the NMR signal attenuation given in Eq. 4 can be used to understand the effects of restricted diffusion in any NMR imaging and spectroscopy pulse sequence that employs gradients that are small enough—a requirement which is common to standard sequences but also desirable when one is interested in characterizing geometric features of small pores or in biological and clinical applications. In this work, we focused on the double-PFG experiments only.

Using the solutions presented above, an apparent or average pore dimension can be estimated even when the pores are not perfectly spherical or cylindrical. If the diffusion time is long enough for the molecules to travel across the longest distance present in the pore and if the pores are randomly oriented, it is appropriate to use the solutions for spherical pores. Otherwise, the results obtained for distribution of cylinders can be expected to yield more meaningful results.

Many different experimental designs are possible for the analysis of double-PFG acquisitions and estimation of a pore size from them. In all our figures, we plotted the NMR signal attenuation vs. angle curves. Estimation of a pore size is possible by directly fitting the relevant expression to such a single angular profile. However, when the SNR is limited, one may have to apply gradients that do not adequately satisfy the $(\gamma\delta Ga)^2 \ll 1$ condition to be able to resolve the angular variation of the signal. The same problem may occur when the size of the pores turns out to be larger than predicted before the acquisition. To alleviate any bias that may be introduced by the higher order terms in this case, data with multiple values of gradient strengths can be acquired. Then the slope of the (ln E) vs. $G^2$ curve at the origin can be estimated (e.g., by fitting a fourth order polynomial, $x_0 G^2 + x_1 G^3 + x_2 G^4$, to the data) along each angle. The resulting profile of slopes can be used in the estimation of a compartment size.

The small $\gamma\delta Ga$ regime considered here is the same one used in Mitra's work as referenced above. The ability to probe restricted diffusion in this regime is desirable in characterizing features of small pores. However, note that, among other conditions, Mitra's results assume infinitesimally short gradient pulses. This assumption alone demands strong gradient strengths when very small pores are to be examined, because the signal should attenuate by an observable amount, i.e., $\gamma\delta Ga$ can not be extremely small due to a finite SNR. However, our formulations do not assume such extreme values for any gradient timings. This ability furthers the feasibility of our approach by incorporating the duration of the gradient pulses, reducing the requirement for large gradient magnitudes.

Note that FIGS. 2A-2C and 5A-5B indicate that deviations from the idealized values for the timing parameters assumed in Mitra's work lead to significant deviations from his formulas. Therefore, the analysis and methods disclosed herein can improve the accuracy of the estimations. Furthermore, because the disclosed approaches permit measurements with arbitrary timing parameters, so that measurement techniques can be more adaptable and increase the dimensionality of the specimen parameter space that can be spanned in diffusion NMR acquisitions while alleviating the stringent hardware requirements inherent in the PFG experiment.

Anisotropy induced by restricting boundaries can be exploited to estimate the orientations perpendicular to the walls of macroscopic pores in single-PFG imaging studies where the voxels are smaller than the pore size. Anisotropy predicted in the double-PFG experiments can be envisioned to arise from the same phenomenon at a much smaller length scale.

Note that different length scales can be probed by varying the diffusion time in single-PFG experiments, as has been done to quantify scaling laws in disordered media. The double-PFG method provides an alternative means to probe multiple length scales, and is capable of elucidating any local order that may be present. In fact, the coexistence of ensemble anisotropy along with microscopic anisotropy, as treated in this disclosure, is an example of how double-PFG can be used to observe phenomena manifested in different length scales.

By observing the dependence of the NMR signal intensity on the angle between the gradients used in the two separate blocks of the double-PFG experiment, restricted diffusion can be observed and distinguished from free or multi-compartmental Gaussian diffusion. Note that the origins of the upward curvature of the single-PFG NMR signal decay vs. $q^2$ (i.e., $E(q^2)$) curves on semi-logarithmic plots observed from tissue samples is a widely debated topic among the biological NMR community. The ability of the double-PFG experiments to discriminate multi-compartmental from restricted diffusion is expected to further our understanding of the determinants of such behavior.

The methods disclosed herein permit many variations in experimental parameters as well as in the specimen under investigation. The disclosed methods are based on a general expression (derived in Appendix A) that enables the evaluation of the effect of restricted diffusion at long wavelengths. While the disclosure provides examples based on double-PFG experiments, similar analyses can be performed using a myriad of pulse sequences. In particular examples, explicit solutions for diffusion taking place between infinite parallel plates as well as in cylindrical and spherical pores are provided and can be used in estimating or otherwise determining specimen properties. The dependence of the signal intensity on the angle between the two gradients of the double-PFG experiments can be interpreted as a signature of local anisotropy induced by macroscopic restrictions. Because the signal is also sensitive to ensemble anisotropy, which may be due to a coherence in the orientations of anisotropic pores, it may be appropriate to extract a term that includes only microscopic anisotropy. This dependence was shown to be identical for anisotropic pores with perfectly isotropic orientation distributions. The disclosed methods can be used to evaluate specimens based on variation of few or many pulse sequence parameters to obtain accurate Information on pore microstructure from double-PFG acquisitions, including compartment size and fiber orientation distributions-all from the long wavelength regime (i.e., the small-q behavior) of the NMR signal attenuation.

II. Diffusion-Diffraction Specimen Analysis

In this section, specimen analysis based on applying the same gradient strength along the direction perpendicular to the boundaries is described, wherein A corresponding to each pair of the pulses is equal. This special case of the N-PFG experiment has been studied to observe the (temporal) frequency dependence of the M signal. See, for Stepisnik and Callaghan, "The long time tail of molecular velocity correlation in a confined fluid: observation by modulated gradient spin-echo NMR," Physica B 292:296-301 (2000) and Stepisnik and Callaghan, "Low-frequency velocity correlation spectrum of fluid in a porous media by modulated gradient spin echo," Magn. Reson. Imaging 19:469-472 (2001). Stapf has proposed a single-shot acquisition of several echoes in such experiments with particular emphasis on obtaining the values of the correlation function at multiple times. See S. Stapf, "Determination of velocity autocorrelation functions by multiple data acquisition in NMR pulsed-field gradient experiments," J. Magn. Reson. 152:308-312 (2001). As disclosed herein, such an N-PFG measurement can yield diffraction-type non-monotonic signal attenuation patterns which are different from the diffraction patterns obtained when a single pair of pulses is used. To produce the signal attenuation curves, the matrix formalism developed by Callaghan can be used, which is based on the idea of representing an arbitrary gradient waveform by a series of impulses. See P. T. Callaghan, "A simple matrix formalism for spin echo analysis of restricted diffusion under generalized gradient waveforms," J. Magn. Reson. 129:74-84 (1997) and Caprihan et al., "A multiple-narrow-pulse approximation for restricted diffusion in a time-varying field gradient," J. Magn. Reson. A 118:94-102 (1996). This approach can be extended to conveniently simulate the signal from multi-PFG experiments in these restricted domains. For convenience, diffusion-diffraction patterns in idealized experimental conditions for diffusion taking place in parallel plane, cylindrical and spherical pores are described. Then diffusion-diffraction in parallel plane pores and the effects of variations of $\Delta$, $\delta$ and $t_m$ on signal attenuation is described. The new diffraction patterns obtained from multi-PFG experiments can improve the feasibility and accuracy of pore size estimation from diffusion/ diffraction-based measurements so that an average pore size can be estimated even in samples containing pores with a broad distribution of sizes.

A. Measurements in "Ideal" Conditions

When the duration of the diffusion gradients ($\delta$) is small compared to the diffusion-time, given by the time delay between the application of the pulses ($\Delta$), the echo attenuation, i.e., the ratio of the diffusion-attenuated signal to the signal obtained when no gradient is applied, in a single-PFG experiment is given by $$E_\Delta(q) = \int dr\, \rho(r) \times \int dr'\, P_\Delta(r,r')\exp(i2\pi q \cdot (r-r')), \quad (28)$$

wherein $\rho(r)$ is the initial spin density, and $P_\Delta(r, r')$ is the propagator indicating the probability of a diffusing particle initially at location r to end up at r' after time $\Delta$. For extreme values of diffusion time, the propagator becomes $$P_0(r, r') = \delta(r-r'), \text{ and} \quad (29)$$

$$P_\infty(r, r') = \rho(r'). \quad (30)$$

Figure 1C:
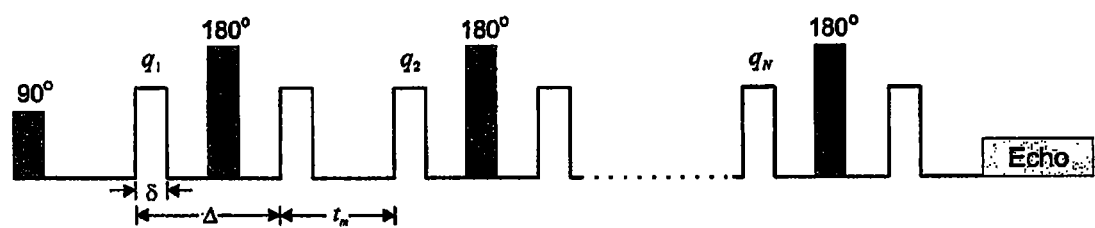
FIG. 1C is a schematic of an N-pulse sequence. The gray boxes depict RF pulses while the blank boxes show gradients. All diffusion pulses have the same duration $\delta$. All N pairs have the same separation $\Delta$, and the consecutive pairs are separated by the same mixing time $t_m$.

Note that this single-PFG experiment is a special case of the experiment in FIG. 1C with $\delta$=0 and N=1.

Next, we shall consider the N-PFG experiment depicted in FIG. 1C with $\delta$=0. We further consider the case in which all diffusion times, gradient strengths and their directions, and mixing times are equal. In this case, there are a total of 2N gradients applied and the signal attenuation is given by $$E_{\Delta,tm}(q,N) = \int dr_1 \rho(r_1) e^{2\pi i q \cdot r_1} \times \int dr_1' P_\Delta(r_1,r_1') e^{-2\pi i q \cdot r_1'} \times \\ \int dr_2 P_{tm}(r_1',r_2) e^{-2\pi i q \cdot r_2} \int dr_2' P_\Delta(r_2,r_2') e^{2\pi i q \cdot r_2'} \times \\ \int dr_N P_{tm}(r_{N-1}',r_N) e^{(-1)^{N-1} 2\pi i q \cdot r_N} \times \int dr_N' P_\Delta(r_N,r_N') \\ e^{(-1)^N 2\pi i q \cdot r_N'} \quad (31)$$

In the limit of infinite diffusion times as well as mixing times, Eq. 30 can be used in all appearances of the propagator in Eq. 31, which results in complete decoupling of all integrations to yield $$E_{\infty,\infty}(q,N) = |S_0(q)|^{2N}, \quad (32)$$

wherein $S_0(q)$ is a structure function given by $$S_0(q) = \int dr\, \rho(r) e^{2\pi i q \cdot r}, \quad (33)$$

and obeys the relation $S_0(-q) = S_0(q)^*$.

When $\rho(r)$ is taken to be equal to the reciprocal of the pore volume inside the pore and 0 elsewhere, the structure function takes the following forms for three simple geometries considered:

$$S_0(q) = \quad (34)$$

$$\begin{cases} \dfrac{\sin(\pi qL)}{\pi qL} e^{i\pi qL}, & \text{parallel plane pore with separation } L \\ \dfrac{J_1(2\pi qr)}{\pi qr}, & \text{cylindrical pore with radius } r \\ \dfrac{3}{(2\pi qR)^2}\left(\dfrac{\sin(2\pi qR)}{2\pi qR} - \cos(2\pi qR)\right), & \text{spherical pore with radius } R \end{cases}$$

This form of the structure function is based on the assumption that the cylindrical and spherical pores are centered at an origin which is defined by a point at which the magnetic field due to the diffusion gradient is zero. In the parallel plane pore, it is assumed that one of the planes passes through the origin and the gradient is applied in a direction perpendicular to the parallel planes. Similarly, for the cylindrical pores, the diffusion gradient is taken to be perpendicular to the cylinder's axis.

Perhaps a more interesting limit is when $\Delta$ is infinite, but the mixing time is 0. In this case, there are a total of N+1 gradient pulses with effective q-values $$q_1=q,\ q_2=-2q,\ q_3=2q, \ldots q_N=(-1)^{N-1}2q,\ q_{N+1}=(-1)^N q, \quad (35)$$

resulting in a signal attenuation of $$E_{\infty,0}(q, N) = \begin{cases} |S_0(q)|^2 |S_0(2q)|^{N-1}, & N\, odd \\ S_0(q)^2 S_0(2q)^* |S_0(2q)|^{N-2}, & N\, even \end{cases} \quad (36)$$

When P number of pores, isolated from each other, contribute to the overall signal, the resulting signal attenuation is given by $$E_{\Delta,t_m}(q, N) = \dfrac{\sum_{k=1}^P V_k E_{\Delta,t_m,k}(q, N)}{\sum_{k=1}^P V_k}, \quad (37)$$

where $E_{\Delta,t_m,k}$ is the signal attenuation from the k-th pore, which depends on its size, and $V_k$ is the volume of the pore, which can be taken to be L, $r^2$ and $R^3$ when, respectively, distributions of parallel plane, cylindrical and spherical pores are concerned.

B. N-PFG Experiment with Arbitrary Timing Parameters

Although the above results are quite instructive, the assumptions regarding the timing parameters are generally not appropriate for practical measurements. The deviations from the ideal parameters typically involve finite values of $\Delta$ and $\delta$. Moreover, although a $t_m$=0 condition can be realized experimentally, this would require application of gradient pulses whose magnitude is twice that of the first and last gradients. Therefore, when the gradient strength is limited, it is beneficial to have a mixing time greater than or equal to $\delta$. To understand the effects of deviations from ideal parameters, we have adapted the matrix formalism developed in Callaghan as referenced above to the disclosed multi-PFG experiments. This implementation followed from Callaghan with one correction on the discretization of finite-width pulses, which is detailed below.

Pulse Discretization

Figure 12A:
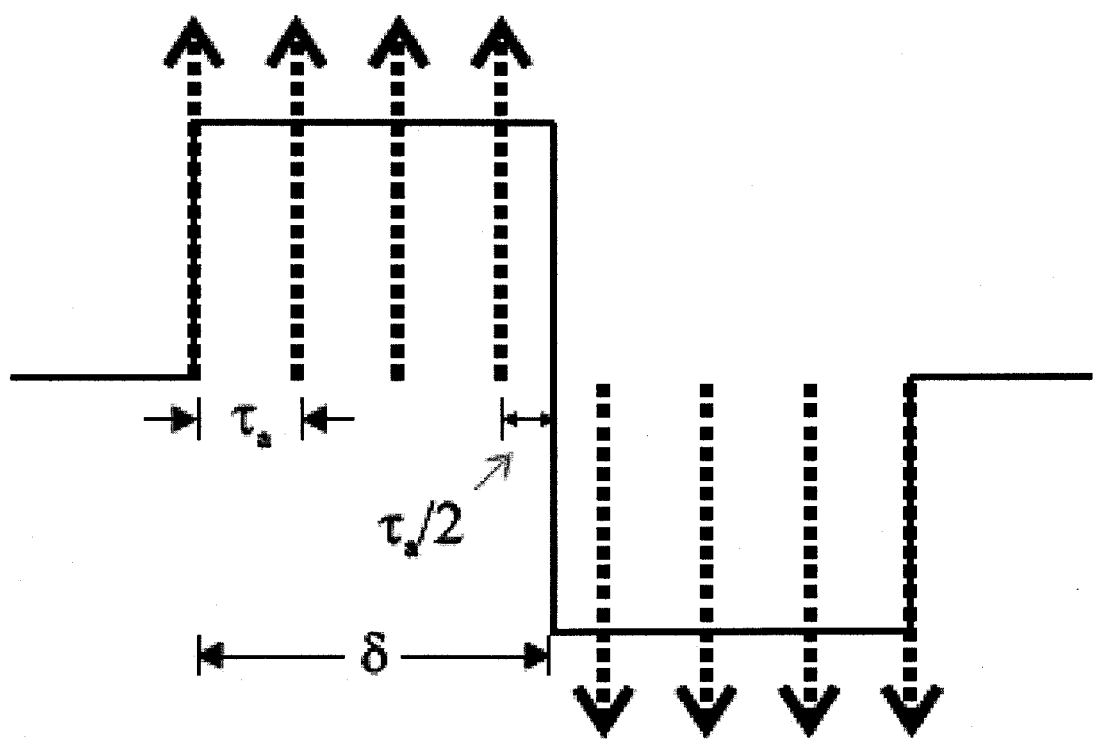
FIGS. 12A-12B illustrate discretization of a steady gradient pulse sequence using the scheme described in Callaghan, "A simple matrix formalism for spin echo analysis of restricted diffusion under generalized gradient waveforms," J. Magn. Reson. 129:74-84 (1997) (FIG. 12A) and an alternative scheme described herein (FIG. 12B).
Figure 12B:
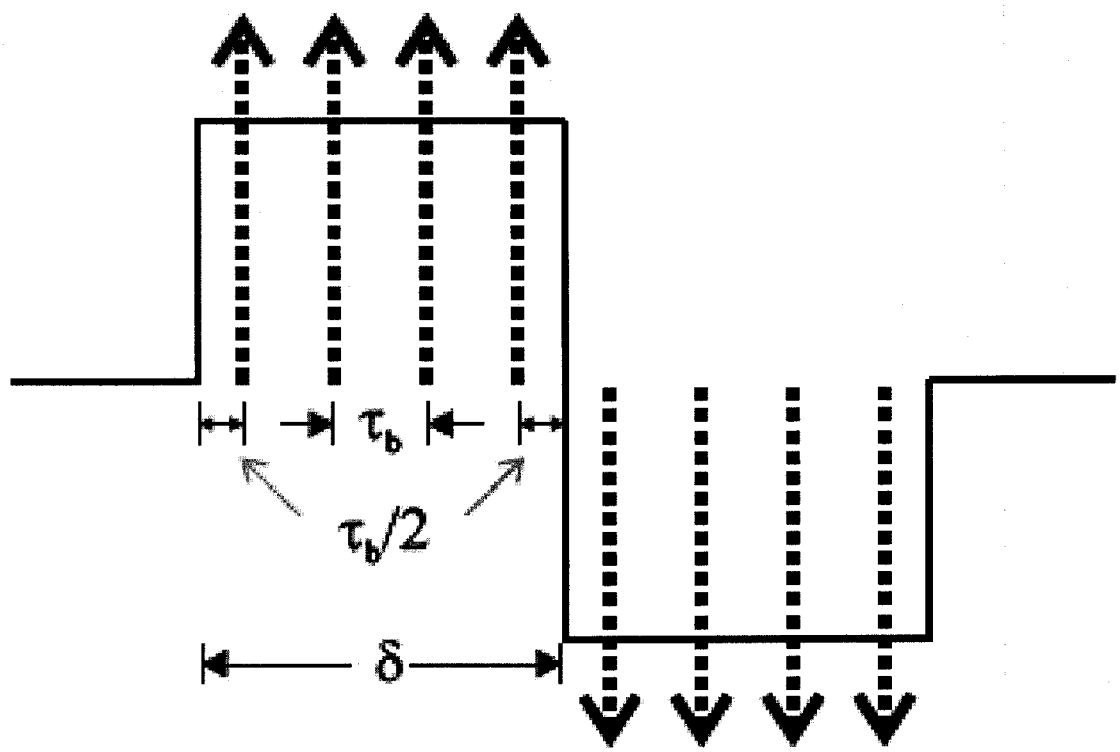

Two different discretizations of finite width gradient pulses are shown in FIGS. 12A-12B wherein FIG. 12A shows the scheme employed in Callaghan and FIG. 12B shows the approach disclosed herein. The pulse sequence is a simple steady gradient spin echo experiment which is a special case of PGSE experiment with $\delta$=$\Delta$. Note that when the number of gradient impulses approximating each of the gradient lobes is set to 1, i.e., when we keep only the first impulse of each gradient lobe, the scheme in FIG. 12A yields a pulse separation value of $\Delta$=$\delta$+$\tau$/2, which is inconsistent with the real diffusion time.

In order to make a more quantitative assessment, we consider the case of Gaussian diffusion with this pulse sequence. Unlike in FIG. 12A, however, we start from a train of M pulses with separation time $\tau$. Note that this same train of impulses can be envisioned to be the discretizations of the steady gradient spin echo experiments with $\delta_a$=(M−½)$\tau$ and $\delta_b$=M$\tau$ according to the schemes in Callaghan and ours respectively. The exact form of the signal attenuation from this experiment is given, after some algebra, by $$E(q) = \exp\left(-\frac{2M^2+1}{3M}4\pi^2 q^2 D\tau\right), \quad (38)$$

where q is the net wave number and D is the diffusion coefficient. Comparing this result with the analytical expression for continuous pulses given by the well-known Stejskal-Tanner formula $E(q)=\exp(-4\pi^2 q^2 D(\Delta-\delta/3))$ with $\Delta=\delta$ suggests that the train of M pulses exactly represents an experiment with an effective pulse duration $$\delta = \left(M + \frac{1}{2M}\right)\tau. \quad (39)$$

Comparing this result with those implied by the two discretization approaches suggests that our discretization depicted in FIG. 12B is more accurate since the true value of $\delta$ in Eq. 39 asymptotically converges to the value of $M_\tau$ from above whereas the value implied by the former approach is smaller than $M_\tau$.

The error caused by the former discretization can be quite significant. For example, consider Gaussian diffusion with $D=2.0\times10^{-3}$ mm$^2$/s observed using the single PFG experiment with $\Delta=\delta=50$ ms, and $q=40$ mm$^{-1}$. If we discretize this pulse sequence with M=10; using the scheme in FIG. 12A, we get a signal value of 0.0116, whereas the discretization in FIG. 12B would yield the approximate value of 0.0145 for the same pulse sequence. Exact result for the signal attenuation implied by the Stejakal-Tanner relation is 0.0148.

C. Diffusion Diffraction Results

FIGS. 7A-7F show simulation results from parallel plane, cylindrical and spherical pores under idealized experimental parameters. The left column (FIGS. 7A-7C) show results with infinite mixing time, whereas the right column (FIGS. 7D-7F) depicts the same for $t_m=0$. It is clear from Eq. 32 that the experiments with higher number of pulse pairs (N) when mixing time is large, simply attenuate the signal even more without adding any new information. The left column confirms this expectation.

The situation is quite different when mixing time is set to 0. There are a number of observations that should be made. First, we shall consider the case when N is odd. When N is greater than 1, Eq. 36 suggests that the echo attenuation from a single-PFG experiment is multiplied by a power of the absolute value of $S_0(2q)$. Since $S_0(q)$ exhibits diffraction dips, $|S_0(2q)|$ has to have similar behavior at exactly half the q-value. This fact is readily observed by comparing the attenuation curves from N=1 with those from N=3. It should also be noted that when N is odd, the signal is real and positive.

Finally, we consider the case when N is even. In this case, the signal can in general be complex. However, since the structure function is the Fourier transform of a real function, when the geometry is symmetric around the plane that goes through the origin and whose normal is parallel to the diffusion gradient, the results will be real. Furthermore, the $S_0(q)^2 S_0(2q)^*$ factor ensures that the resulting signal will be real even when $S_0(q)$ is complex, as long as the geometry has a symmetry plane perpendicular to the direction of the gradient. This is the case for the parallel plane pore that we study. The signal may be negative valued though. In our plots, negative values are flipped, but assigned a dotted line to discriminate them from the positive sections of the curves represented by continuous lines. Note that Eq. 36 does have the $S_0(2g)$ factor, indicating that the compartment size can be estimated using half the gradient strength. In this case, however, the signal crosses into negative values rather than bouncing bark up. Note that there are significant qualitative differences between the signal curves obtained from different geometries. The signal decay curves obtained from cylindrical and spherical pores possess extra lobes when compared to the curves from parallel planes when N is greater than 1. The signal vanishes when gr={0.305, 0.558, 0.610, ... } for the cylindrical pore and qR={0.358, 0.601, 0.715, ... } for the spherical pore.

FIGS. 8A-8F show signal attenuation curves when a distribution of isolated pores with varying dimensions are considered. In these simulations we have assumed that the dimensions are Gaussian distributed with mean values of $L_0$, $R_0$ and standard deviations of $\sigma_L$, $\sigma_R$ for the parallel plane and spherical pore ensembles respectively. Note that as the distribution of pore sizes gets broader, the diffraction dips disappear in single-PFG experiments. A similar response is observed when experiments with other odd number of pulse pairs are simulated. However, when the number of pulse pairs is even, especially the first diffraction dip is well preserved although its location may suffer slight shifts. This is due to the fact that the "dips" for even N are characterized by zero crossings. Consequently, when the q-value is close to its zero-crossing value, the contribution of the pores whose sizes are smaller than what is implied by the zero crossing will be positive whereas the contribution from larger pores will be negative. These two groups of contributions will cancel each other maintaining the zero crossing. There are two competing effects that try to shift the zero crossing away from its position implied by a homogeneous distribution of pores. The larger pores contain more spines than the smaller pores. This is why the signal attenuations are multiplied by the pore volume in Eq. 37. This effect pushes the zero crossings to the left. However, diffusion inside larger pores gives rise to more rapid signal attenuation, which acts in the opposite fashion. As seen in the second row of FIGS. 8A-8F (i.e., FIGS. 8B, 8E), in the simulations we have performed, the latter effect seems to influence the signal more than the former. However, the location of the first zero-crossing seems to remain very close to the point implied by the mean value of the pore size even when the standard deviation is large.

Next, we focus on the parallel plane pore and investigate the effects of variations in $\Delta$. The results for experiments from N=1 through N=6 are shown in FIGS. 9A-9F. Similar to the $t_m\to\infty$ case, increasing N beyond N=3 does not create any change other than attenuating the signals more. The straightening of the single-PFG curve for smaller values of $\Delta$ is observed in a similar fashion in other odd values of N. When N is even, the features of the curves are more resilient to the decreases in $\Delta$. This is because the zero crossings do not disappear readily in the attenuation curves. The first of these crossings appear to occur at slightly larger values of q when $\Delta$ is reduced.

Figure 10C:
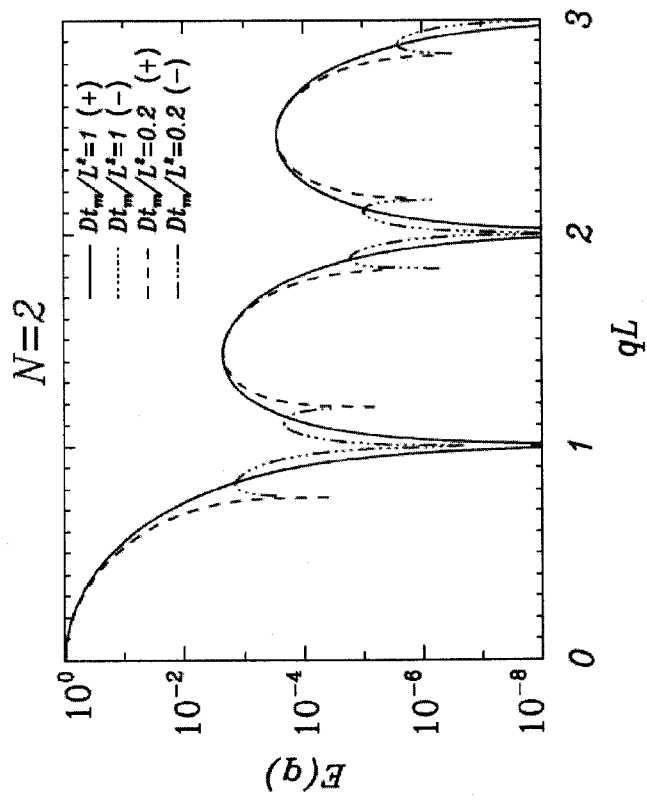
FIGS. 10A-10D illustrate signal attenuation as a function of q with varying values of $t_m$ for the parallel plane pore. $\delta=0$, $D\Delta/L^2=2$. The left column (FIGS. 10A-10B) shows the attenuation curves when $t_m$ is small, where the right column (FIGS. 10C-10D) show the same for large values of $t_m$.
Figure 10A:
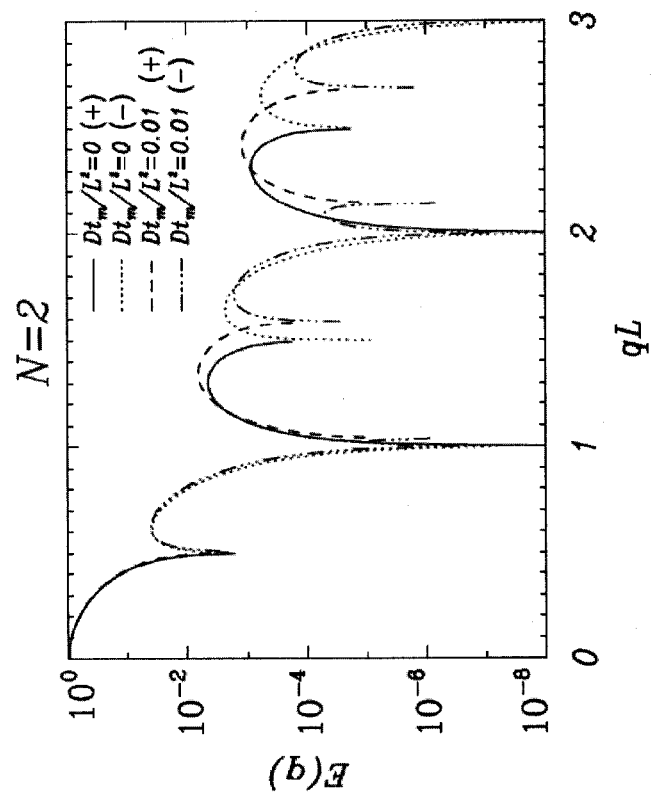
Figure 10D:
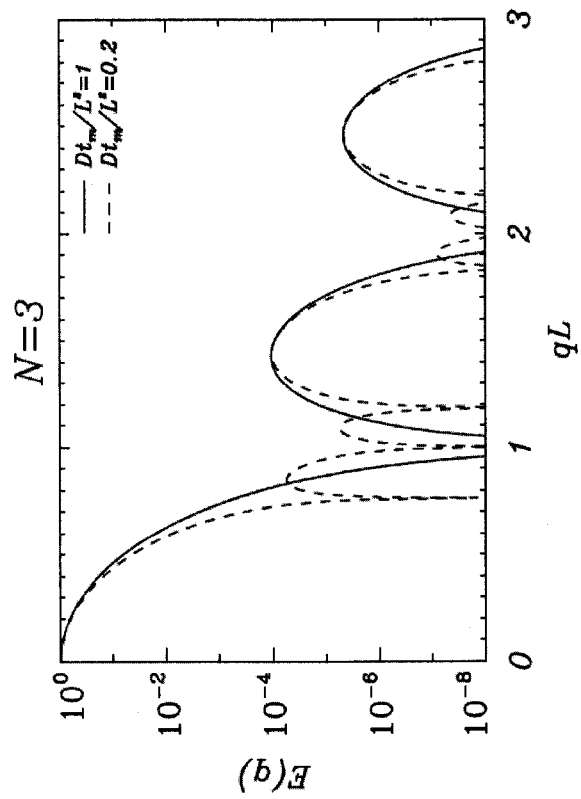
Figure 10B:
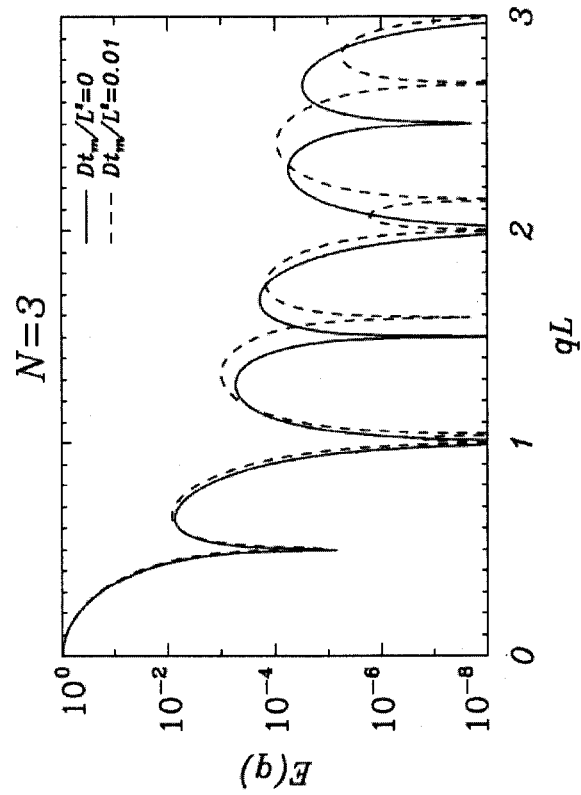
Figure 11D:
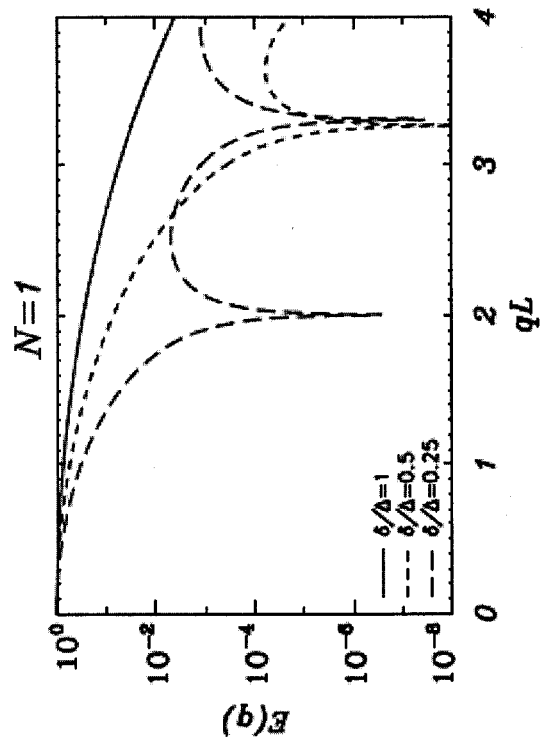
FIGS. 11A-11F illustrate signal attenuation as a function of q with varying values of $\delta$ for the parallel plane pore. $t_m=0$, $D\Delta/L^2=2$. The left column (FIGS. 11A-11C) show the attenuation curves when $\delta$ is small, where the right column (FIGS. 11D-11F) show the same for larger values of $\delta$.
Figure 11A:
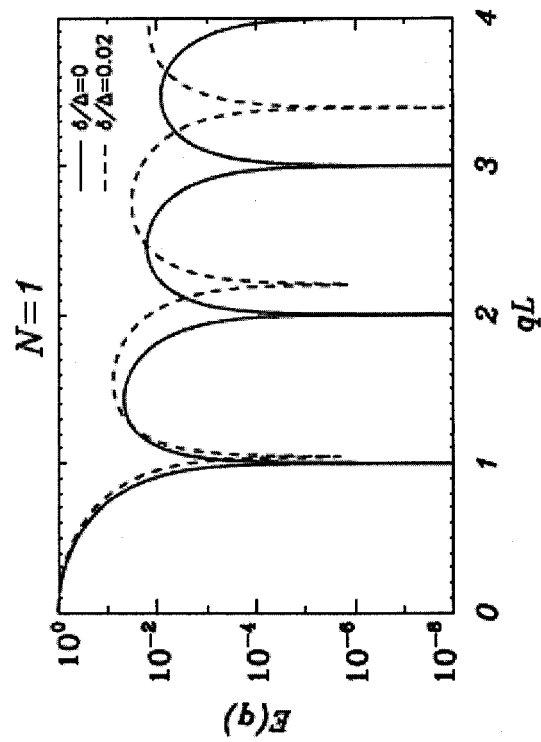
Figure 11E:
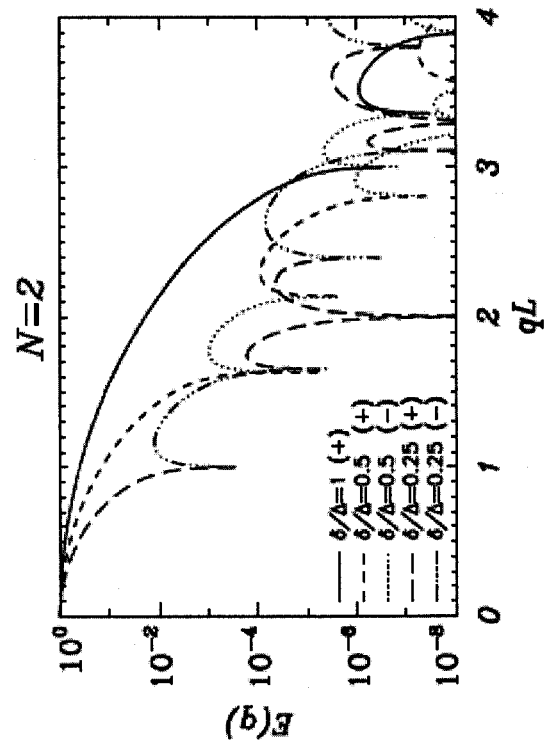
Figure 11B:
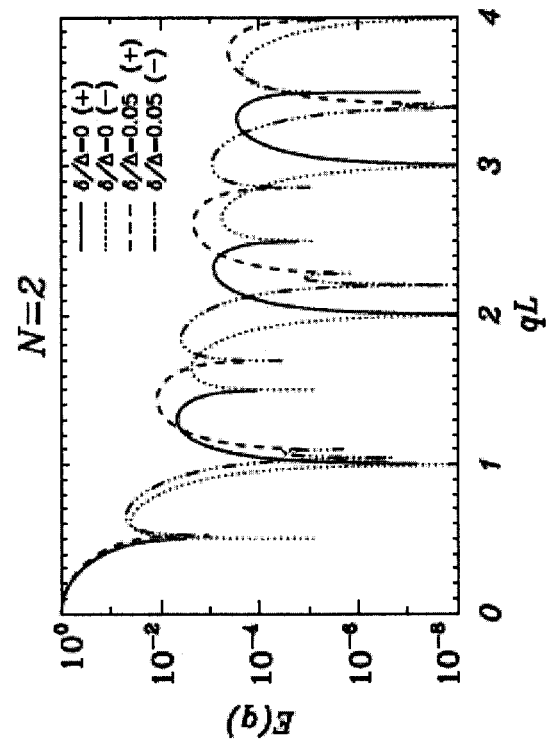
Figure 11F:
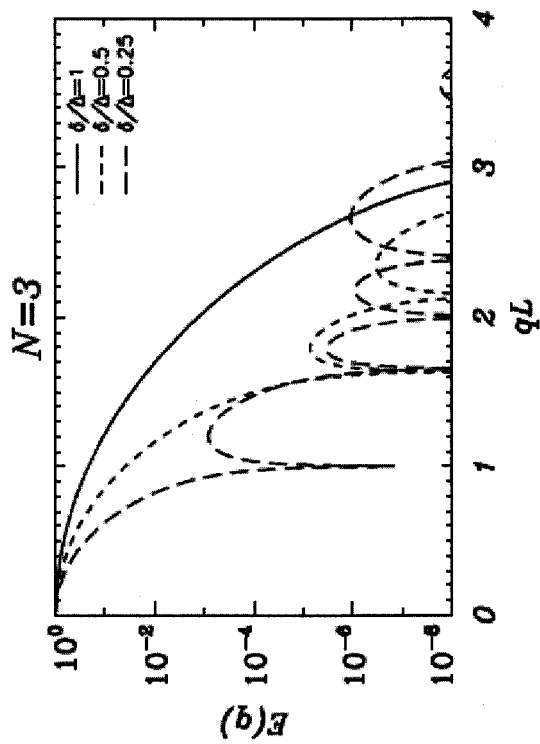
Figure 11C:
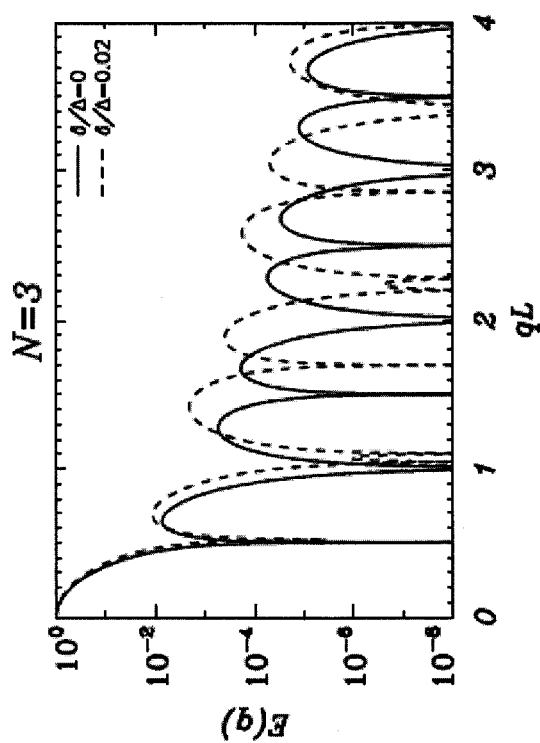

Another timing parameter that can be changed in multi-PFG experiments is the mixing time $t_m$. Since it is not defined in single-PFG experiments, we provide results from double- and triple-PFG experiments only. The left column of FIGS. 10A-10D (i.e., FIGS. 10A, 10B) shows the results when $t_m$ is increased from the value of 0. This is important because the $t_m=0$ condition necessitate the application of twice the gradient strength which may not be affordable especially when one is interested in measuring the sizes of smaller pores. If this is the case, then the minimum value of $t_m$ can be equal to $\delta$. The results indicate that the first few lobes of the attenuation curves are quite robust to the variations in $t_m$ although significant alterations are observed at higher q-values. Progressively increasing $t_m$ pushes the zero crossings towards the locations of diffraction wells observed when N=1. The locations of these do not change at all. When $t_m$ gets very large, zero crossings reach these points. This is the case when the diffusional processes in different sections of the multi-PFG experiment become completely independent from one another. In this case, the diffraction patterns become similar to those from single-PFG experiments although experiments with larger number of gradient pairs suffer more signal loss.

Finally, N-PFG experiment with finite sized gradient pulses are considered. In finite-pulsewidth single-PFG experiments, the diffusion signal appears as if the motion of spins takes place between the two centers-of-mass of the particles calculated during the application of the diffusion pulses. Therefore, the pore appears to be smaller than its actual size resulting in a shift of the diffraction dips towards higher q-values. As shown in FIGS. 11A-11F, as the pulse width increases, the same effect is observed in multi-PFG experiments.

The formulations and the simulations presented above demonstrate that the non-monotonic behavior of the signal attenuation from N-PFG experiments leads to significant advantages in the determination of compartment sizes when compared to those from single-PFG experiments. An estimate for the compartment sizes can be obtained by determining the locations (q-values) at which the signal is lost or substantially reduced in magnitude. The reciprocal of the q-values that yield the diffraction dips, upon multiplication of the expected values of qL, qr or qR as described above, gives the estimate for the compartment size. If the experimental parameters differ from the ideal conditions, then the values of qL, qr and qR can be modified accordingly.

Since the diffraction patterns have different characteristics when different numbers of pulse pairs (N) are employed, it may be beneficial to repeat the experiment with different number of pulse pairs. An alternative is to simply acquire the signal obtained at different refocussing times during a single scan. In either case, obtaining a hierarchy of signals can improve the identification of different diffraction dips.

Despite the significant improvements the N-PFG experiment offers, it has some disadvantages. The predicted signal values when N>1 are smaller than those from single-PFG experiments necessitating higher signal-to-noise-ratios (SNRs). This may be alleviated to certain extent by using smaller $\Delta$ values and even number of gradient pulse pairs (see FIGS. 9A-9F and related discussion). Also note that, when N is even, the signal is predicted to be negative and possibly complex. Therefore magnitude-valued data can not illustrate the zero-crossings. However, upon taking the magnitude value of the signal, the zero-crossings turn into dips, which can still be employed in the compartment size estimation.

More information can be obtained from the signal attenuation curves by transforming the signal decay profiles into higher-dimensional joint probability density functions, which could suggest an alternative explanation to the origins of the predicted diffraction patterns by illustrating the correlations of molecular motion between the separate encoding intervals.

The diffraction patterns of multi-PFG experiments with small mixing times are qualitatively different from those obtained via single-PFG experiments. These differences can yield significant improvements in the feasibility of acquisitions and widen the range of potential applications of the diffraction patterns. Specifically, the first diffraction dip generally occurs at exactly half the q-value when compared with diffraction patterns from single-PFG experiments. This makes it possible to measure smaller pore sizes and make the pore size estimates more accurate as pulses of half the width can be applied. Moreover, the diffraction pattern is different when obtained from different pore shapes, which can be exploited to infer the shapes of the pores. When an even number of gradient pulse pairs is used, diffraction patterns can be observed at shorter diffusion times; this in turn makes the experiments more practical, reduces the total acquisition time and makes it possible to measure large pore sizes. Finally, an average compartment size can be estimated from samples with a broad distribution of pore sizes using the multi-PFG technique with an even number of pulse pairs.

III. Compartment Distributions

In many clinical and other applications, a distribution of compartment properties (such as size, diffusivity shape, orientation, volume, area, spin fraction) can serve as a convenient indicator of specimen structure for living or other specimens. For example, evaluations of nerve function in humans or other animals can be based on a distribution of axon diameters. In other examples, other size parameters such as length, width, radius, or other dimensions of spheres, rectangles, or other shapes having curved, elliptical, rectangular, polygonal, ovoid, or other cross-sectional shapes can be evaluated. Such distributions and evaluations based on such distributions can permit diagnosis or treatment in medical applications. An observed magnetic resonance signal can be expressed as a sum of contributions from restricted and hindered population fractions.

In typical examples, the numbers of terms in the sums can be limited by noting values of n and k for which contributions become sufficiently small. While in some examples, the population fraction can be assumed to have a particular functional form, for example, a gamma-function, in other examples, a population function can be obtained from the signals directly without imposing a particular functional form on the population. Such methods and apparatus are referred to as parametric and non-parametric, respectively. In some examples, parameters associated with the distribution can be obtained and used for evaluation. For example, a mean determined based on a gamma distribution can be used, or other combinations of distribution parameters or moments including mean, mean square, and higher order moments can be estimated and used to diagnose or otherwise characterize a specimen.

Electromagnetic signals obtained by application of one or more static or time-varying magnetic fields to a specimen such as double PFG sequences described above can be processed and recorded. In many examples, such electromagnetic signals are detected with one or more field coils, amplified, filtered, or otherwise processed, digitized, and recorded in one or more computer-readable media as one or more digital values. Processing of such electromagnetic signals can be performed either prior to digitization or after digitization, or both, as is convenient. Processing in a general purpose or special purpose computer based on stored computer-executable processing instructions is convenient. As used herein, "recorded signals" refers to digital or other stored representations of such electromagnetic signals. Such recorded signals can be transmitted, displayed, or otherwise provided for specimen evaluation. As used herein, computer readable media include various types of memory (ROM, RAM) as well as floppy disks, hard disks, and other storage media.

Parametric methods can be based on any form of distribution deemed convenient. For example, Gaussian, gamma function, log-normal; or other distributions can be used. In some examples, determination of distribution parameters can serve as a basis for specimen evaluation and treatment. In other examples, moments of a distribution such a mean, mean square, or higher order moments can be determined, and specimen evaluations based on such determinations. Distribution parameters can also be used in segmenting, classifying or clustering tissues into regions having specific properties. Classifying, clustering, or other evaluations can be based on algorithms such the k-means algorithms or others. They can be used to perform hypothesis tests to make determinations and distinctions between different voxels or tissue regions. Typically parameters of restricted or hindered compartments, distributions of such parameters, moments of such distributions, or other specimen evaluations are stored locally in a memory or communicated via a display or other visual device, an audio device, or via a network such as a local area network, a wide area network such as the Internet, or otherwise provided for clinical or other applications. Specimen images can be based on restricted compartment sizes, size distribution, orientation, or orientation distributions. Instructions for executing such methods on computer can be implemented in high or low level computer languages such as C++ or using an analysis environment such as provided by MATH-CAD, MATHEMATICA, or MATLAB.

The methods disclosed herein can be used to interrogate specimens having hindered or restricted compartments having different properties along one or more directions as well as specimens in which such compartments are spherical or other shapes having little or no directionality.

Evaluation of restricted compartment properties and distributions of restricted compartments can be used in diagnosis and treatment of conditions associated with degeneration or other changes in restricted compartment properties. For example, axon dimensions and distributions can be associated with nervous system function and used in the assessment of Alzheimer's disease, Parkinson's disease, or others. The disclosed methods can also be used to follow normal and abnormal development in the nervous system and in muscles in which water is also trapped within impermeable cells. It can be used generally to follow changes in disease, degeneration, and aging in the nervous system.

Appendix A: Modeling of NMR Signal Attenuation

A representative mathematical treatment of NMR signal attenuation from restricted geometries at long diffusion wavelengths is provided in this Appendix. The diffusion propagator $P(r, r', t)$, denotes the displacement probability from the location r to r' during a time interval t and is the solution to the diffusion equation $$D_0 \nabla'^2 P(r, r', t) = \frac{\partial P}{\partial t}, \quad \text{(A1)}$$

subject to the initial condition $P(r, r', 0) = \delta(r-r')$ and the boundary condition $\hat{n} \cdot \nabla P(r, r', t)|_{r \in \Sigma} = 0$ in pores with non-relaxing impermeable walls, where $\hat{n}$ is the direction perpendicular to the interface, $\Sigma$, at location r. A convenient representation of the diffusion propagator is given by $$P(r, r', t) = \sum_{n=0}^{\infty} e^{-\lambda_n t} u_n(r) u_n^*(r'), \quad \text{(A2)}$$

where $u_n(r)$ is an eigenfunction of the Laplacian operator with the eigenvalue $-\lambda_n/D_0$. The long diffusion-time asymptotics of the propagator requires one of the eigenvalues to be 0. If this eigenvalue is denoted with index 0, then $u_0(r) = V^{-1/2}$, where V is the pore volume.

In this Appendix, we consider a general gradient waveform as shown in FIGS. 1A-1B. As proposed in Caprihan et al., J. Magn Reson. A 118, page 94 (1996), the gradient profile can be approximated by a train of impulses. We adopt the discretization suggested in Ozarslan and Basser, J. Magn. Reson. 188, page 285 (2007), where the time axis is divided into M intervals of duration $\tau$ and the i-th impulse ($1 \leq i \leq M$) is assumed to be applied at time $t_i$—the middle point of its respective interval. Then the magnitude of the impulse in the i-th interval is taken to be $$q_i = \frac{\gamma}{2\pi} \int_{t_i - \tau/2}^{t_i + \tau/2} G(t) dt, \quad \text{(A3)}$$

where $\gamma$ is the gyromagnetic ratio of the spins, and G(t) is the time-dependent effective gradient waveform.

It was shown that using the eigenfunction expansion of the propagator as in Eq. A2, the NMR signal attenuation can be expressed as a matrix product. See, for example, P. T. Callaghan, J. Magn. Reson. 129, page 74 (1997).

$$\tilde{E} = S^T(q_1) R(\tau) A(q_2) R(\tau) A(q_3) R(\tau) \ldots R(\tau) A(q_{M-1}) R(\tau) S^*(-q_M). \quad \text{(A4)}$$

Note that $\tilde{E}$ is an approximation to the true NMR signal attenuation, denoted by E, where any discrepancy between the two is due to the "time-slicing" employed in the construction of the matrix product scheme. Our approach to deriving a general expression for the signal attenuation involves evaluating $\tilde{E}$, and subsequently, taking the limit of the resulting expression as $\tau \to 0$, $M \to \infty$, while $M\tau = T$, similar to what is done in path integral (functional integration) methods.

In Eq. A4, S is an M-dimensional vector whose $k^{th}$ component is given by the following integral over the pore volume, V, $$S_k(q) = V^{-1/2} \int_V u_k(r) e^{i 2\pi q \cdot r} dr. \quad \text{(A5)}$$

Throughout this Appendix, the left subscript c in an expression $_cX(q)$ will denote the term proportional to $(2\pi q a)^c$ in a Taylor series expansion of the quantity X around $q=0$, where a is a characteristic length in the pore space. With this convention, it is straightforward to show that the vector S satisfies the relationships $$_c S_k(-q) = (-1)^c {_c S_k(q)}, \quad \text{(A6a)}$$

$$_0 S_k(q) = \delta_{0k}. \quad \text{(A6b)}$$

Similarly, A is an M×M matrix with components $$A_{km}(q) = \int_V u_k^*(r) u_m(r) e^{i 2\pi q \cdot r} dr. \quad \text{(A7)}$$

Clearly, A satisfies the useful relationships:

$$A(-q) = A^\dagger(q), \quad \text{(A8a)}$$

$$A_{0m}(q) = S_m(q), \quad \text{(A8b)}$$

$$A_{k0}(q) = S_k^*(-q), \quad \text{(A8c)}$$

$$_0 A_{km}(q) = \delta_{km}. \quad \text{(A8d)}$$

Finally, R is an M×M diagonal matrix with components $$R_{km}(t) = e^{-\lambda_k t} \delta_{km}, \quad \text{(A9)}$$

where the first element of R is unity, i.e., $R_{00} = 1$. Note that both A and R satisfy the semigroup property, i.e., $$A(q_1) A(q_2) = A(q_1 + q_2), \quad \text{(A10a)}$$

$$R(t_1) R(t_2) = R(t_1 + t_2). \quad \text{(A10b)}$$

We are primarily interested in evaluating the signal attenuation value given in Eq. A4 up to the terms of order $(4\pi^2 M^2 |q_j||q_j|a^2)$. For this purpose, the following relationships $$_0 A(q_a) R(t)_c S^*(q_b) = R(t)_c S^*(q_b), \quad (A11a)$$

$$_c S^T(q_a) R(t)_0 A^*(q_b) = _c S^T(q_a) R^*(t), \quad (A11b)$$

$$_c A(q_a) R(t)_0 S^*(q_b) = _c S^*(-q_a), \quad (A11c)$$

$$_0 S^T(q_a) R(t)_c A(q_b) = _c S^T(q_b) \quad (A11d)$$

are helpful in simplifying the form of the matrix product in Eq. A4. The $0^{th}$ order term of E is given by $$_0 E = _0 S^T(q_1) R((M-1)\tau)_0 S^*(-q_M) = 1. \quad (A12)$$

The expression $$_0 S^T(q_a) R(t)_1 S^*(q_b) = -i \frac{2\pi}{V} q_b \cdot r_{cm} \quad (A13)$$

is useful in evaluating the first order term, given by $$_1 \tilde{E} = i \frac{2\pi}{V} r_{cm} \cdot \sum_{j=1}^{M} q_j. \quad (A14)$$

Inserting Eq. A3 into the above expression yields $$_1 E = i \frac{\gamma}{V} r_{cm} \cdot \int_0^T G(t) dt, \quad (A15)$$

where $r_{cm}$ is the center-of-mass of the pore. When the integral above vanishes at the echo time, no contribution to the NMR signal is expected from the first order term.

For the second order term of the echo attenuation, one needs the quantities $$e_{20} = _2 S^T(q_a) R(t)_0 S^*(q_b) = -\frac{2\pi^2}{V} \int_V (q_a \cdot r)^2 dr, \quad (A16)$$

and $$e_{11} = _1 S^T(q_a) R(t)_1 S^*(q_b) \quad (A17)$$
$$= \frac{4\pi^2}{V} \int_V dr q_a \cdot r \int_V dr' q_b \cdot r' P(r, r', t).$$

The exact forms of $e_{20}$ and $e_{11}$ depend on the particular shape of the pore under consideration. Many pores of interest can be taken to be approximately isotropic. In fact, the pores commonly treated in the literature (i.e., parallel plates and cylindrical and spherical pores), are simply isotropic pores in one-, two- and three-dimensions, respectively. If we take the radii of the cylindrical and spherical pores to be a, and the separation between the two infinite plates to be 2a, then the above integrals can be given by the unified expressions $$e_{20} = -\frac{2\pi^2 q_a^2 a^2}{(2+D)}, \quad (A18)$$

and

-continued $$e_{11} = 8\pi^2 a^2 q_a \cdot q_b \sum_{n=1}^{\infty} s_{Dn} e^{-\omega_{Dn}(t_b - t_a)}. \quad (A19)$$

Here, D is the dimension of the isotropic pore, and $$\omega_{Dn} = \frac{\alpha_{Dn}^2 D_0}{a^2}, \quad (A20)$$

where $\alpha_{1n} = (n - \tfrac{1}{2})\pi$, and $\alpha_{2n}$ and $\alpha_{3n}$ satisfy the expressions $J_1'(\alpha_{2n}) = 0$ and $j_1'(\alpha_{3n}) = 0$, respectively. Here, $J_1(x)$ is the first order Bessel function and $j_i(x)$ is the first order spherical Bessel function.

The quantity $S_{Dn}$ is given by $$s_{Dn} = \frac{1}{\alpha_{Dn}^2 (\alpha_{Dn}^2 - D + 1)}. \quad (A21)$$

Note that $S_{Dn}$ satisfy the relationship $$\sum_{n=1}^{\infty} s_{Dn} = \frac{1}{2(2+D)}, \quad (A22)$$

which can be established using Laplace transform techniques, or more simply by writing down the matrix product representation of the NMR signal (up to the quadratic term) for a single-PFG experiment in the narrow pulse regime and setting its $\Delta \to 0$ limit to 1.

These results can be combined to yield the following convenient form for the quadratic term of the NMR signal attenuation for a generalized gradient waveform $$_2 \tilde{E} = -4\pi^2 a^2 \sum_{j=1}^{M} \sum_{k=1}^{M} q_j \cdot q_k \sum_{n=1}^{\infty} s_{Dn} e^{-\omega_{Dn} |t_k - t_j|}. \quad (A23)$$

Inserting Eq. A3 into the above expression twice, and taking the $\tau \to 0$ limit, yields $$_2 E = -2\gamma^2 a^2 \sum_{n=1}^{\infty} s_{Dn} \int_0^T dt e^{\omega_{Dn} t} G(t) \cdot F_{Dn}(t), \quad (A24)$$

where $$F_{Dn}(t) = \int_t^T G(t') e^{-\omega_{Dn} t'} dt'. \quad (A25)$$

Therefore, the NMR signal at long diffusion wavelengths can be written as $E \cong _0 E + _1 E + _2 E$, where the terms in this expression are provided in Eqs. A12, A15 and A24. When the integral of the effective gradient waveform vanishes, as is the case in the versions of the double-PFG experiment described herein, the first order term is zero and the NMR signal attenuation is given by Eq. 4.

This derivation demonstrates that the matrix product formalism developed by P. T. Callaghan, J. Magn. Reson. 129, page 74 (1997), along with the discretization scheme in Ozarslan and Basser, J. Magn. Reson. 188, page 285 (2007), can be used as analytical tools for the derivation of NMR signal intensity obtained using generalized gradient waveforms.

What is claimed is:

1. At least one computer readable medium not consisting of a signal having stored thereon computer-executable instructions for a method of generating an estimate of a distribution of restricted compartment sizes within a sample, comprising:
obtaining, from a magnetic resonance imaging apparatus, a recorded magnetic resonance signal amplitude as a function of magnetic resonance wavevector in response to a multi-PFG sequence that includes at least two PFG sequences; and generating the estimate of the distribution of restricted compartment sizes occurring within the sample based on determination of a magnetic resonance wavenumber magnitude associated with a local minimum value of the recorded magnetic resonance signal amplitude, or a determination of a magnetic resonance wavenumber magnitude associated with a transition in the recorded magnetic resonance signal amplitude occurring between a positive value and negative value.

2. The at least one computer readable medium of claim 1, wherein the method also comprises providing an estimate of a mean value of a restricted compartment size distribution.

3. The at least one computer readable medium of claim 2, wherein the multi-PFG sequence includes an odd number of PFG sequences.

4. The at least one computer readable medium of claim 2, wherein the multi-PFG sequence includes an even number of PFG sequences.

5. The at least one computer readable medium of claim 2, wherein the mean value is associated with a radius of cylindrical, or a radius of spherical restricted compartments, or a separation of planar compartments.

6. The at least one computer readable medium of claim 1, wherein the PFG sequences of the multi-PFG sequence have common effective gradient magnitudes.

7. A method of generating an estimate of a distribution of restricted compartment sizes within a sample, comprising:
receiving from a magnetic resonance imaging apparatus a recorded magnetic resonance signal amplitude responsive to a multi-PFG sequence; and
based on the recorded magnetic resonance signal amplitude, providing an estimate of at least one size characteristic of a distribution of restricted compartments occurring within a specimen, wherein the estimate is associated with a mean value of a size distribution and is based on a magnetic resonance wavenumber magnitude associated with a local minimum value of the recorded magnetic resonance signal amplitude, or a transition of the recorded magnetic resonance signal amplitude occurring between a positive value and a negative value.

8. A method of generating an estimate of a distribution of restricted compartment dimensions within a sample, comprising:
applying, with a magnetic resonance imaging apparatus, at least a first PFG sequence and a second PFG sequence to a specimen, wherein the first and second sequences are applied with a plurality of angles between field gradients of the first and second sequences;
recording a magnetic resonance signal amplitude as a function of the plurality of angles;
determining a magnetic resonance wavenumber magnitude associated with a local minimum value of the recorded magnetic resonance signal amplitude or determining a magnetic resonance wavenumber magnitude associated with a transition in the recorded magnetic resonance signal amplitude occuring between a positive value and a negative value; and
based on the determining, providing the estimate of the restricted compartment dimensions occurring within the specimen.

9. The method of claim 8, wherein the dimension is associated with a diffusion distance that is a function of a diffusion constant in the restricted compartment.

10. The method of claim 8, further comprising providing an estimate of a single restricted compartment orientation based on the recorded magnetic resonance signal.

11. The method of claim 10, further comprising providing estimates of restricted compartment orientations for at least first and second restricted compartment distributions.

12. The method of claim 11, further comprising displaying an image based on restricted compartment properties as a function of specimen location with a display device.

13. The method of claim 8, wherein the dimension is associated with a radius of a spherical, or a radius of a cylindrical restricted compartment.

14. The method of claim 8, wherein the applied field gradients are selected in order to ensure that a product of magnetic resonance wavenumbers and the estimated dimension is less than 0.5.

15. The method of claim 8, wherein the recorded signals are associated with a plurality of mixing times, or diffusion times.

16. The method of claim 8, further comprising obtaining a distribution associated with orientations of a plurality of restricted compartments.

* * * * *